US012575828B2

(12) United States Patent
Prudden et al.

(10) Patent No.: US 12,575,828 B2
(45) Date of Patent: Mar. 17, 2026

(54) THREADED ANCHOR ADVANCER

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: John Prudden, Manchester, MA (US); Nehal N. Patel, Boston, MA (US)

(73) Assignees: Smith & Nephew, Inc.; Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 72 days.

(21) Appl. No.: 18/650,628

(22) Filed: Apr. 30, 2024

(65) Prior Publication Data

US 2024/0366219 A1     Nov. 7, 2024

Related U.S. Application Data

(60) Provisional application No. 63/463,209, filed on May 1, 2023.

(51) Int. Cl.
| | |
|---|---|
| *A61B 17/068* | (2006.01) |
| *A61F 2/08* | (2006.01) |
| *A61B 17/00* | (2006.01) |

(52) U.S. Cl.
CPC ........ *A61B 17/0682* (2013.01); *A61F 2/0811* (2013.01); *A61B 2017/00743* (2013.01);
(Continued)

(58) Field of Classification Search
CPC ....... A61B 17/0682; A61B 2017/00743; A61F 2/0811; A61F 2002/0817; A61F 2002/0858
See application file for complete search history.

(56) References Cited

U.S. PATENT DOCUMENTS

| | | | |
|---|---|---|---|
| 3,650,453 A | 3/1972 | Smith, Jr. | |
| 4,043,504 A | 8/1977 | Hueil et al. | |
| | (Continued) | | |

FOREIGN PATENT DOCUMENTS

| | | |
|---|---|---|
| CN | 105596044 B | 1/2019 |
| WO | 2021262575 A1 | 12/2021 |
| | (Continued) | |

*Primary Examiner* — Phong Son H Dang
(74) *Attorney, Agent, or Firm* — Seager, Tufte & Wickhem LLP

(57) ABSTRACT

A surgical anchor delivery device includes a shaft, a plurality of anchors disposed within the shaft, and a threaded rod disposed within the shaft and threadably engaged with the anchors. Rotation of the threaded rod advances the anchors toward the distal end of the shaft without rotating the anchors relative to the shaft. The delivery device may include an actuation mechanism configured to rotate the threaded rod. A method of delivering the anchors may include advancing the distal end of the shaft to a first location, rotating the threaded rod to advance a first anchor out the distal end of the shaft without rotating the first anchor relative to the shaft, repositioning the distal end of the shaft to a second position, and rotating the threaded rod to advance a second anchor out the distal end of the shaft without rotating the second anchor relative to the shaft.

14 Claims, 27 Drawing Sheets

(52) U.S. Cl.
CPC ................. *A61F 2002/0817* (2013.01); *A61F 2002/0858* (2013.01)

(56) References Cited

U.S. PATENT DOCUMENTS

| | | | |
|---|---|---|---|
| 4,403,693 A | 9/1983 | Froehlich | |
| 4,454,875 A | 6/1984 | Pratt et al. | |
| 4,478,362 A | 10/1984 | Foslien | |
| 4,523,707 A | 6/1985 | Blake, III et al. | |
| 4,527,726 A | 7/1985 | Assell et al. | |
| 4,618,086 A | 10/1986 | Li et al. | |
| 4,787,387 A | 11/1988 | Burbank, III et al. | |
| 4,951,860 A | 8/1990 | Peters et al. | |
| 5,038,991 A | 8/1991 | Thornton | |
| 5,089,009 A | 2/1992 | Green | |
| 5,114,065 A | 5/1992 | Storace | |
| 5,170,926 A | 12/1992 | Ruckdeschel et al. | |
| 5,258,010 A | 11/1993 | Green et al. | |
| 5,425,490 A | 6/1995 | Goble et al. | |
| 5,643,319 A | 7/1997 | Green et al. | |
| 5,667,513 A | 9/1997 | Torrie et al. | |
| 5,725,554 A | 3/1998 | Simon et al. | |
| 5,911,353 A | 6/1999 | Bolanos et al. | |
| 5,997,552 A | 12/1999 | Person et al. | |
| 6,146,387 A | 11/2000 | Trott et al. | |
| 6,277,131 B1 | 8/2001 | Kalikow | |
| 6,296,641 B2 | 10/2001 | Burkhead et al. | |
| 6,352,541 B1 | 3/2002 | Kienzle et al. | |
| 6,572,626 B1 * | 6/2003 | Knodel .............. A61B 17/0682 |
| | | | 606/151 |
| 6,779,701 B2 | 8/2004 | Bailly et al. | |
| 7,214,232 B2 | 5/2007 | Bowman et al. | |
| 7,473,258 B2 | 1/2009 | Clauson et al. | |
| 7,530,484 B1 | 5/2009 | Durrani | |
| 7,533,790 B1 | 5/2009 | Knodel et al. | |
| 7,753,250 B2 | 7/2010 | Clauson et al. | |
| 7,862,573 B2 | 1/2011 | Darois et al. | |
| 7,926,692 B2 | 4/2011 | Racenet et al. | |
| 7,954,683 B1 | 6/2011 | Knodel et al. | |
| 7,963,432 B2 | 6/2011 | Knodel et al. | |
| 8,056,789 B1 | 11/2011 | White et al. | |
| 8,066,720 B2 | 11/2011 | Knodel et al. | |
| 8,220,690 B2 | 7/2012 | Hess et al. | |
| 8,240,538 B1 | 8/2012 | Manoux | |
| 8,261,958 B1 | 9/2012 | Knodel | |
| 8,317,072 B1 | 11/2012 | Knodel et al. | |
| 8,602,286 B2 | 12/2013 | Crainich et al. | |
| 8,668,718 B2 | 3/2014 | Euteneuer et al. | |
| 8,733,616 B2 | 5/2014 | Bailly et al. | |
| 8,763,878 B2 | 7/2014 | Euteneuer et al. | |
| 8,821,536 B2 | 9/2014 | Euteneuer et al. | |
| 8,821,537 B2 | 9/2014 | Euteneuer et al. | |
| 8,840,642 B2 | 9/2014 | Euteneuer et al. | |
| 8,870,049 B2 | 10/2014 | Amid et al. | |
| 8,888,798 B2 | 11/2014 | Bourque et al. | |
| 8,920,464 B2 | 12/2014 | Euteneuer et al. | |
| 8,939,343 B2 | 1/2015 | Milliman et al. | |
| 9,027,819 B2 | 5/2015 | Euteneuer et al. | |
| 9,033,201 B2 | 5/2015 | Euteneuer | |
| 9,095,337 B2 | 8/2015 | Euteneuer et al. | |
| 9,107,661 B2 | 8/2015 | Euteneuer et al. | |
| 9,125,650 B2 | 9/2015 | Euteneuer et al. | |
| 9,198,704 B2 | 12/2015 | Sack et al. | |
| 9,247,978 B2 | 2/2016 | Euteneuer et al. | |
| 9,259,220 B2 | 2/2016 | Euteneuer et al. | |
| 9,271,726 B2 | 3/2016 | Euteneuer | |
| 9,314,235 B2 | 4/2016 | Bojarski et al. | |
| 9,351,733 B2 * | 5/2016 | Fischvogt .............. A61B 17/10 |
| 9,364,216 B2 | 6/2016 | Rockrohr et al. | |
| 9,364,240 B2 | 6/2016 | Whitfield et al. | |
| 9,370,356 B2 | 6/2016 | Euteneuer et al. | |
| 9,486,218 B2 | 11/2016 | Criscuolo et al. | |
| 9,675,346 B2 | 6/2017 | Euteneuer et al. | |
| 9,713,468 B2 | 7/2017 | Harris et al. | |
| 9,717,490 B2 | 8/2017 | Deitch | |

| | | | |
|---|---|---|---|
| 9,924,934 B2 | 3/2018 | Housman | |
| 10,039,545 B2 | 8/2018 | Sadowski et al. | |
| 10,123,796 B2 | 11/2018 | Westling et al. | |
| 10,179,015 B2 | 1/2019 | Lavigne et al. | |
| 10,314,689 B2 | 6/2019 | Zenz-Olson et al. | |
| 10,463,368 B2 | 11/2019 | Kostrzewski | |
| 10,470,761 B2 | 11/2019 | Morgan et al. | |
| 10,524,794 B2 | 1/2020 | Bolduc et al. | |
| 10,743,855 B2 | 8/2020 | Nguyen et al. | |
| 11,051,808 B2 * | 7/2021 | Euteneuer .......... A61B 17/0642 |
| 11,116,500 B2 * | 9/2021 | Cloutier ................ A61F 2/0063 |
| 2001/0004693 A1 | 6/2001 | Burkhead et al. | |
| 2002/0169452 A1 | 11/2002 | Tormala et al. | |
| 2002/0188301 A1 | 12/2002 | Dallara et al. | |
| 2003/0009441 A1 | 1/2003 | Holsten et al. | |
| 2003/0187465 A1 | 10/2003 | Bailly et al. | |
| 2004/0097971 A1 | 5/2004 | Hughett | |
| 2004/0153074 A1 | 8/2004 | Bojarski et al. | |
| 2004/0243139 A1 * | 12/2004 | Lewis ................ A61B 17/8891 |
| | | | 606/301 |
| 2005/0075654 A1 | 4/2005 | Kelleher | |
| 2007/0075115 A1 | 4/2007 | Olson et al. | |
| 2007/0250064 A1 | 10/2007 | Darois et al. | |
| 2008/0078807 A1 | 4/2008 | Hess et al. | |
| 2008/0288004 A1 | 11/2008 | Schendel | |
| 2009/0018553 A1 | 1/2009 | Mclean et al. | |
| 2009/0112234 A1 | 4/2009 | Crainich et al. | |
| 2009/0118734 A1 | 5/2009 | Bhatnagar et al. | |
| 2010/0057102 A1 | 3/2010 | Sorrentino et al. | |
| 2010/0057103 A1 | 3/2010 | Sorrentino et al. | |
| 2010/0130989 A1 | 5/2010 | Bourque et al. | |
| 2010/0198192 A1 | 8/2010 | Serina et al. | |
| 2010/0292713 A1 | 11/2010 | Cohn et al. | |
| 2010/0292715 A1 | 11/2010 | Nering et al. | |
| 2010/0312250 A1 | 12/2010 | Euteneuer et al. | |
| 2011/0022065 A1 * | 1/2011 | Shipp ................. A61B 17/0644 |
| | | | 606/151 |
| 2011/0071578 A1 * | 3/2011 | Colesanti ............ A61B 17/064 |
| | | | 606/305 |
| 2011/0079627 A1 | 4/2011 | Cardinale et al. | |
| 2011/0276062 A1 | 11/2011 | Bolduc | |
| 2012/0022557 A1 | 1/2012 | Cabiri et al. | |
| 2012/0211543 A1 | 8/2012 | Euteneuer | |
| 2013/0131700 A1 * | 5/2013 | Criscuolo .............. A61B 17/72 |
| | | | 606/139 |
| 2013/0178871 A1 | 7/2013 | Koogle, Jr. et al. | |
| 2013/0245627 A1 | 9/2013 | Euteneuer et al. | |
| 2013/0245682 A1 | 9/2013 | Euteneuer et al. | |
| 2014/0025082 A1 | 1/2014 | Sack et al. | |
| 2014/0172016 A1 | 6/2014 | Housman | |
| 2014/0200587 A1 * | 7/2014 | Pompee ............. A61B 17/8872 |
| | | | 606/104 |
| 2014/0243855 A1 * | 8/2014 | Sholev ................. A61B 17/068 |
| | | | 606/139 |
| 2014/0276972 A1 * | 9/2014 | Abuzaina ............... A61B 17/08 |
| | | | 606/143 |
| 2015/0142016 A1 | 5/2015 | Bolduc et al. | |
| 2015/0150558 A1 * | 6/2015 | Zergiebel ............. A61B 17/105 |
| | | | 606/139 |
| 2015/0216521 A1 | 8/2015 | Deitch | |
| 2015/0238190 A1 | 8/2015 | Euteneuer | |
| 2015/0272573 A1 | 10/2015 | Euteneuer et al. | |
| 2015/0272584 A1 | 10/2015 | Taylor | |
| 2015/0327858 A1 | 11/2015 | Euteneuer et al. | |
| 2016/0074034 A1 * | 3/2016 | Shipp .................... A61F 2/0063 |
| | | | 606/139 |
| 2016/0100870 A1 | 4/2016 | Lavigne et al. | |
| 2016/0100935 A1 | 4/2016 | Euteneuer et al. | |
| 2016/0120538 A1 | 5/2016 | Westling et al. | |
| 2016/0120542 A1 | 5/2016 | Westling et al. | |
| 2016/0166255 A1 * | 6/2016 | Fischvogt ........... A61B 17/068 |
| | | | 606/139 |
| 2016/0242766 A1 | 8/2016 | Sun et al. | |
| 2016/0262747 A1 | 9/2016 | Euteneuer et al. | |
| 2017/0128068 A1 * | 5/2017 | Zhang ................. A61B 17/064 |
| 2017/0189014 A1 | 7/2017 | Zenz-Olson et al. | |

(56)                    References Cited

U.S. PATENT DOCUMENTS

| | | |
|---|---|---|
| 2018/0028169 A1 | 2/2018 | Bourque |
| 2018/0125474 A1 | 5/2018 | Dougherty et al. |
| 2023/0263615 A1 | 8/2023 | Grabinsky et al. |

FOREIGN PATENT DOCUMENTS

| | | | |
|---|---|---|---|
| WO | 2024054550 | A2 | 3/2024 |
| WO | 20240545550 | A3 | 3/2024 |

* cited by examiner

THREADED ANCHOR ADVANCER

CROSS REFERENCE TO RELATED APPLICATIONS

This application claims the benefit of U.S. Provisional Patent Application Ser. No. 63/463,209 filed on May 1, 2023, the disclosure of which is incorporated herein by reference.

TECHNICAL FIELD

The present disclosure pertains generally to medical devices and methods of using medical devices. More particularly, the present disclosure relates to medical devices and/or systems, and methods of using the same, for arthroscopic placement of multiple surgical anchors in the area of a full or partial thickness tear of a tendon, such as the supraspinatus tendon of the shoulder.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Current procedures for treatment of a torn tendon include affixing a biocompatible implant over the torn tendon. There is an ongoing need to deliver and adequately secure medical implants during an arthroscopic procedure in order to treat injuries to the rotator cuff, rotator cuff tendons, or other soft tissue or tendon injuries throughout a body.

SUMMARY

In one example, a surgical anchor delivery device may comprise an elongate shaft having a lumen extending to a distal end of the elongate shaft, a plurality of surgical anchors disposed within the lumen, and a threaded rod disposed within the elongate shaft and threadably engaged with the plurality of surgical anchors. Rotation of the threaded rod may advance the plurality of surgical anchors within the lumen toward the distal end of the elongate shaft without rotating the plurality of surgical anchors relative to the elongate shaft.

In addition or alternatively to any example described herein, the plurality of surgical anchors is prevented from rotating relative to the elongate shaft.

In addition or alternatively to any example described herein, the lumen includes a noncircular cross-sectional shape.

In addition or alternatively to any example described herein, each surgical anchor of the plurality of surgical anchors includes a noncircular perimeter shape.

In addition or alternatively to any example described herein, each surgical anchor of the plurality of surgical anchors includes a tab extending radially outward from a peripheral edge of the anchor.

In addition or alternatively to any example described herein, the elongate shaft includes a channel extending longitudinally along a wall of the elongate shaft and opening radially inwards.

In addition or alternatively to any example described herein, the tab is configured to extend into the channel when the plurality of surgical anchors is disposed within the lumen.

In addition or alternatively to any example described herein, the plurality of surgical anchors is configured to slide distally within the lumen in response to rotation of the threaded rod.

In addition or alternatively to any example described herein, rotation of the threaded rod is configured to advance the plurality of surgical anchors out of the lumen.

In addition or alternatively to any example described herein, rotation of the threaded rod is configured to drive at least one barb extending distally from each surgical anchor of the plurality of surgical anchors into a target tissue.

In addition or alternatively to any example described herein, a surgical anchor delivery device may comprise a handle including an actuation mechanism, an elongate shaft extending from the handle, the elongate shaft having a lumen extending to a distal end of the elongate shaft, a plurality of surgical anchors disposed within the lumen, and a threaded rod disposed within the lumen and threadably engaged with the plurality of surgical anchors. Rotation of the threaded rod may advance the plurality of surgical anchors within the lumen toward the distal end of the elongate shaft without rotating the plurality of surgical anchors relative to the elongate shaft. The actuation mechanism may be configured to rotate the threaded rod.

In addition or alternatively to any example described herein, the actuation mechanism is configured to rotate the threaded rod in only a single direction.

In addition or alternatively to any example described herein, the actuation mechanism is configured to shift between a starting position and an ending position.

In addition or alternatively to any example described herein, shifting the actuation mechanism from the starting position to the ending position advances only one surgical anchor of the plurality of surgical anchors out of the lumen.

In addition or alternatively to any example described herein, after reaching the ending position, the actuation mechanism disengages from the threaded rod and the actuation mechanism is configured to return to the starting position while disengaged from the threaded rod.

In addition or alternatively to any example described herein, after reaching the ending position, the actuation mechanism is configured to return to the starting position while simultaneously advancing a successive surgical anchor of the plurality of surgical anchors toward the distal end of the elongate shaft without rotating any of the plurality of surgical anchors relative to the elongate shaft.

In addition or alternatively to any example described herein, a method of delivering a plurality of surgical anchors to a treatment site may comprise advancing a distal end of an elongate shaft of a surgical anchor delivery device to a first location at the treatment site, rotating a threaded rod disposed within the elongate shaft in a first direction to advance a first surgical anchor of the plurality of surgical anchors out the distal end of the elongate shaft without rotating the first surgical anchor relative to the elongate shaft, repositioning the distal end of the elongate shaft to a second position at the treatment site, and rotating the threaded rod disposed within the elongate shaft in the first direction to advance a second surgical anchor of the plurality of surgical anchors out the distal end of the elongate shaft without rotating the second surgical anchor relative to the elongate shaft.

In addition or alternatively to any example described herein, the plurality of surgical anchors is disposed within the elongate shaft prior to advancing the distal end of the elongate shaft to the first location.

In addition or alternatively to any example described herein, the threaded rod is only rotatable in the first direction.

In addition or alternatively to any example described herein, rotating the threaded rod includes shifting an actuation mechanism of the surgical anchor delivery device from a starting position to an ending position.

In addition or alternatively to any example described herein, the method may further comprise: after rotating the threaded rod disposed within the elongate shaft in the first direction to advance the first surgical anchor of the plurality of surgical anchors out the distal end of the elongate shaft, resetting the actuation mechanism from the ending position to the starting position before rotating the threaded rod disposed within the elongate shaft in the first direction to advance the second surgical anchor of the plurality of surgical anchors out the distal end of the elongate shaft.

In addition or alternatively to any example described herein, the threaded rod does not rotate while resetting the actuation mechanism from the ending position to the starting position.

The above summary of some embodiments, aspects, and/or examples is not intended to describe each disclosed embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which.

Figure 1:
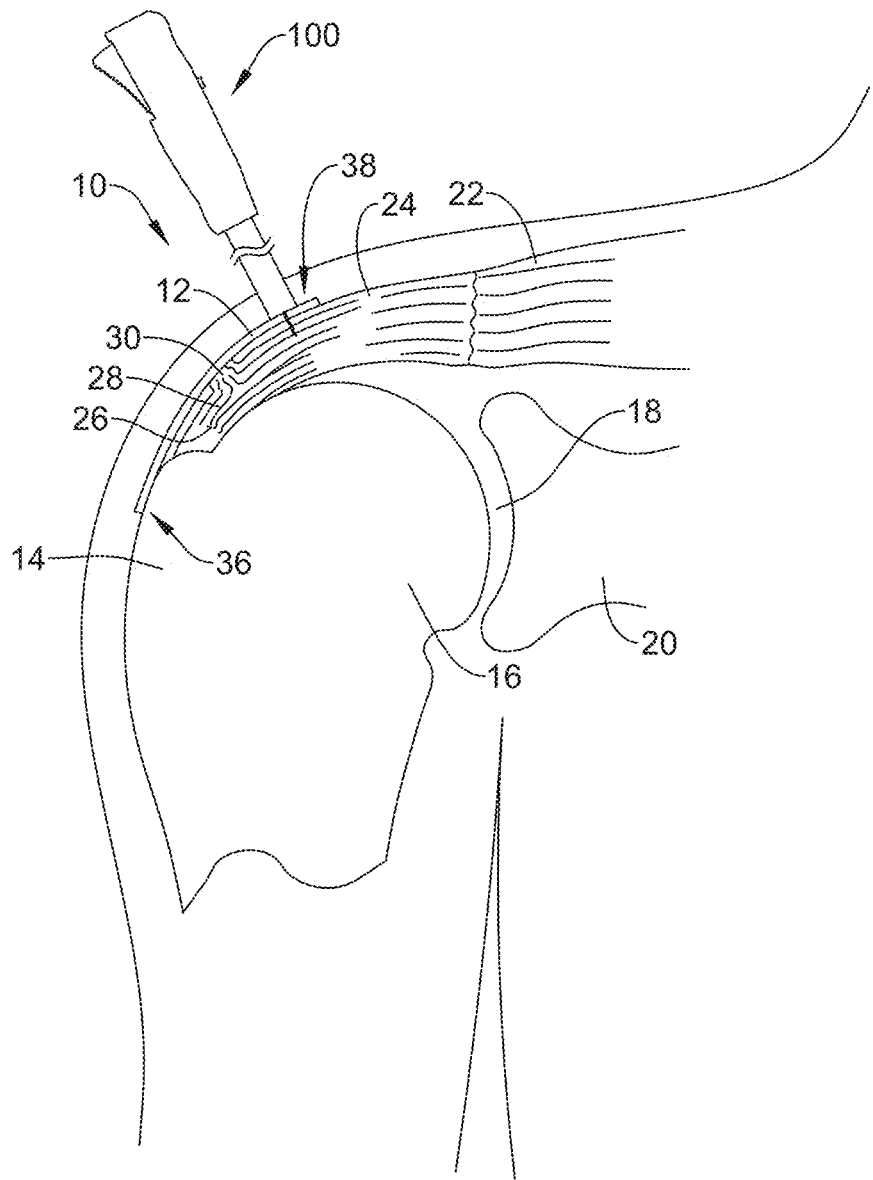
FIGS. 1-2 schematically illustrate a surgical anchor delivery device positioned at a treatment site affixing an implant to a tendon.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale. Like reference numerals indicate like elements throughout the views. The detailed description and drawings are intended to illustrate but not limit the disclosure. Those skilled in the art will recognize that the various elements described and/or shown may be arranged in various combinations and configurations without departing from the scope of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, enlightened by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include one or more particular features, structures, and/or characteristics. However, such recitations do not necessarily mean that all embodiments include the particular features, structures, and/or characteristics. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, individual elements described herein, even if not explicitly shown in a particular combination, are contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures generally illustrate selected components and/or arrangements of medical devices, systems, and/or methods. It should be noted that in any given figure, some features may not be shown, or may be shown schematically, for simplicity. Additional details regarding some elements may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to features or elements may be equally referred to all instances and quantities beyond one of said feature or element. As such, it will be understood that the following discussion may apply equally to any and/or all of the elements for which there are more than one within the medical devices, systems, and/or methods, unless explicitly stated to the contrary. Additionally, all instances of some elements or features may not be shown in each figure for clarity.

With its complexity, range of motion, and extensive use, a common soft tissue injury is damage to the rotator cuff or rotator cuff tendons. Damage to the rotator cuff is a potentially serious medical condition that may occur during hyperextension, from an acute traumatic tear, or from overuse of the joint. An accepted treatment for rotator cuff tears may include reattaching the torn tendon to the humeral head using sutures. Additionally, in treating rotator cuff tears, an accepted practice may also include the placement of a scaffold over the repaired tendon to mechanically reinforce the repaired tendon and/or to promote tissue reformation. Therefore, there is an ongoing need to deliver, position, and secure medical implants to soft tissue during an arthroscopic procedure in order to treat injuries to the rotator cuff, rotator cuff tendons, or other soft tissue or tendon injuries throughout a body. At least some of those procedures may involve the placement of multiple surgical anchors, and in some cases may involve multiple surgical anchor delivery devices. Repeatedly removing a surgical anchor delivery device to load a new surgical anchor onto the surgical anchor delivery device and then reinserting a surgical anchor delivery device to the treatment site to deliver surgical anchors thereto may extend a procedure, may create opportunity to drop a surgical anchor delivery device thereby causing the surgical anchor delivery device to become unsterile, may cause discomfort to the patient, and/or may cause or aggravate other risks. There is an ongoing need to deliver multiple surgical anchors within a single procedure without exchanging the surgical anchor delivery device and/or removing the surgical anchor delivery device between deployment of surgical anchors.

Figure 2:
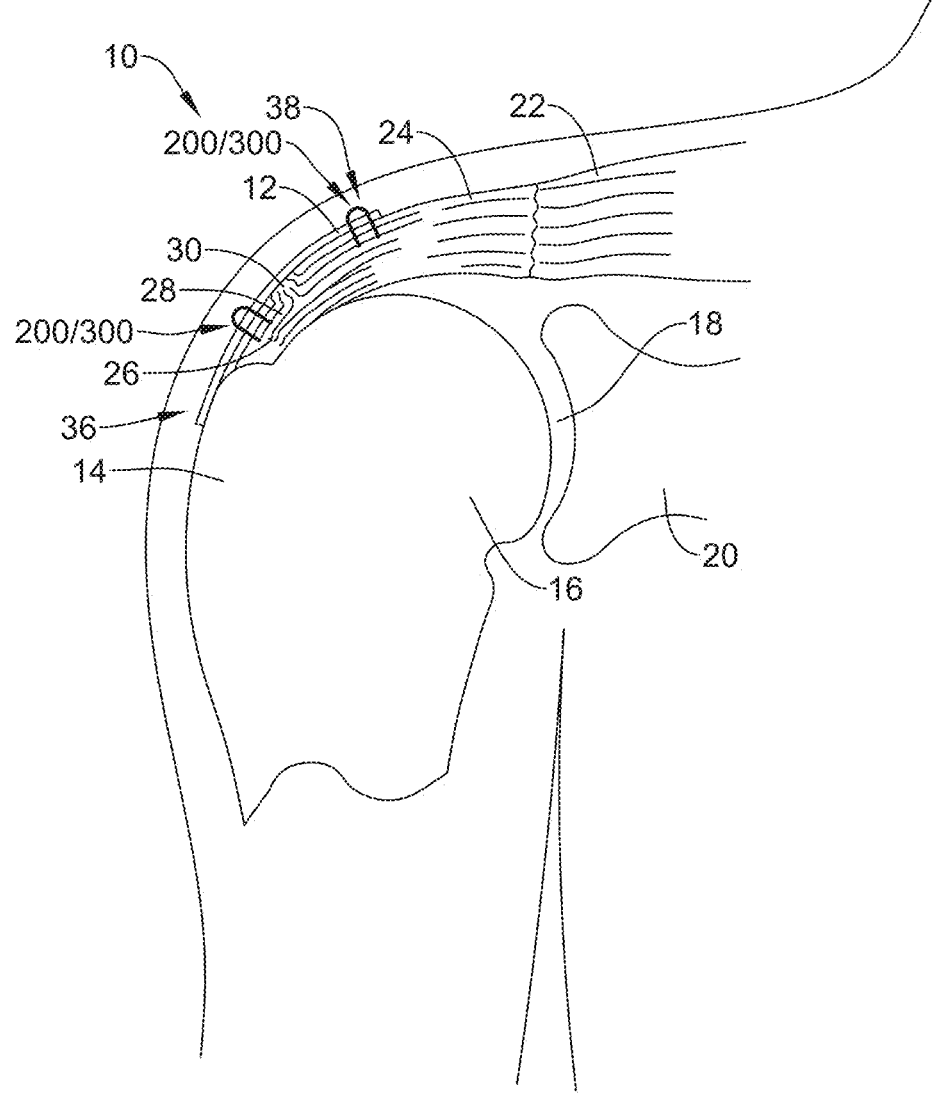

FIGS. 1 and 2 schematically illustrate selected aspects of a shoulder 10 including an implant 12 positioned at a treatment site. In at least some embodiments, the implant 12 may be a sheet-like implant and/or a scaffold configured to reinforce the damaged tissue. In some embodiments, the implant 12 may include collagen and/or may be collagen based. FIGS. 1 and 2 further illustrate a head 14 of the humerus 16 mating with a glenoid fossa 18 of the scapula 20. The glenoid fossa 18 includes a shallow depression in the scapula 20. A supraspinatus tendon 22 is also shown. A distal tendon 24 of the supraspinatus tendon 22 meets the humerus 16 at an insertion point 26.

In FIGS. 1 and 2, the distal tendon 24 includes a damaged portion 28 located near the insertion point 26. The damaged portion 28 includes a tear 30 extending partially through the distal tendon 24. In some cases, the tear 30 may be a partial thickness tear. In some cases, the tear 30 may be a complete thickness tear. The tear 30 is depicted on the bursal side of the distal tendon 24, however, the tear 30 may also be on the opposite or articular side of the distal tendon 24 and/or may include internal tears to the distal tendon 24 not visible on either surface.

FIGS. 1 and 2 illustrate that the implant 12 has been placed over the tear 30. In this example, the implant 12 is placed on the bursal side of the distal tendon 24 regardless of whether the tear is on the bursal side, the articular side, or within the distal tendon 24. Further, the implant 12 may overlay multiple tears.

In some instances, delivery of the implant 12 to a treatment site of a patient may require a physician to create an incision in the patient (e.g., in the patient's skin, etc.) sufficient to access the treatment site. After creating this "access site," the physician may insert an implant delivery system through the incision and/or the access site and position the distal end of the implant delivery system adjacent the treatment site. The physician may then manipulate the implant delivery system to deploy the implant 12 at and/or adjacent the treatment site.

When positioning the implant 12 at and/or adjacent the treatment site, a user may orient the implant 12 such that a proximal portion 36 may be adjacent (e.g., overlaid) on a portion of the humerus 16 (e.g., on the bone), while a distal portion 38 of the implant 12 may overlay the distal tendon 24. Further, once the implant 12 has been placed appropriately, it may be desirable to utilize a surgical anchor delivery device 100 to insert a surgical anchor (or multiple surgical anchors) of a plurality of surgical anchors 200 (e.g., FIG. 5-8) or a surgical anchor (or multiple surgical anchors) of a plurality of surgical anchors 300 (e.g., FIGS. 9-10), as seen in FIG. 2 for example, through the implant 12 into the distal tendon 24 and/or the humerus 16.

In some embodiments, an access sheath may be used during advancement of the surgical anchor delivery device 100 to the treatment site. The access sheath may cover a distal end region of the surgical anchor delivery device 100, thereby shielding portions of the shoulder 10 from edges and/or sharp portions of the surgical anchor delivery device 100 as a distal end of the surgical anchor delivery device 100 is advanced to the treatment site and/or positioned adjacent the implant 12.

Returning briefly to FIG. 1, the surgical anchor delivery device 100 is positioned adjacent to the implant 12. In at least some embodiments, once the surgical anchor delivery device 100 and the access sheath (where present) has been inserted through the incision and/or the access site and advanced to the treatment site, the access sheath may be removed. Removing the access sheath may expose portions of the surgical anchor delivery device 100 which may be utilized to affix the implant 12 to the humerus 16 and/or the distal tendon 24. For example, the implant 12 may be anchored to the humerus 16 using one or more bone anchors and/or the implant 12 may be anchored to the distal tendon 24 using a plurality of surgical anchors 200/300 arranged around a periphery of the implant 12.

Figure 3:
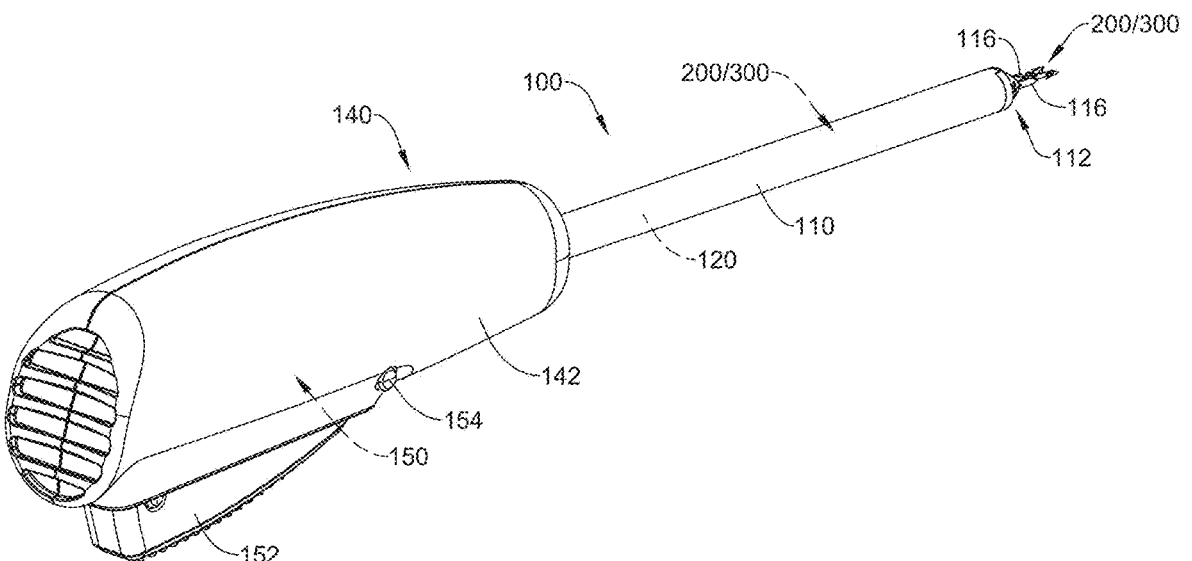
FIG. 3 illustrates selected aspects of a surgical anchor delivery device.
Figure 4:
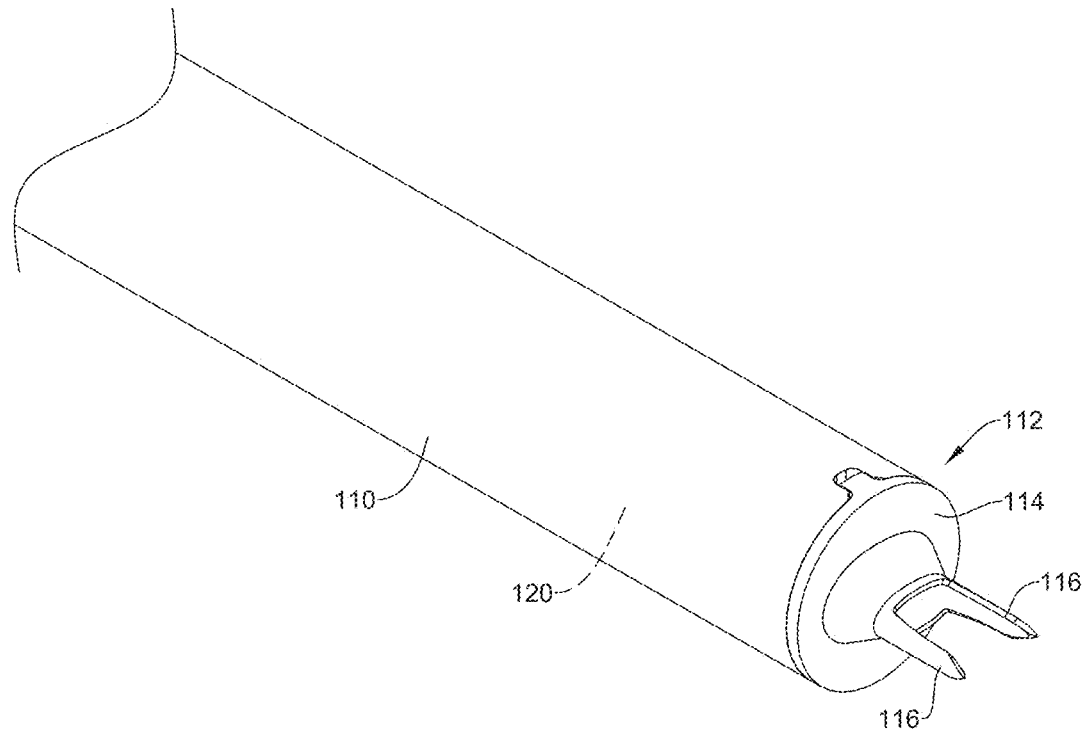
FIG. 4 illustrates selected aspects of the surgical anchor delivery device.

Turning now to FIGS. 3-4, the surgical anchor delivery device 100 may comprise an elongate shaft 110 having a lumen 120 extending therein to a distal end 112 of the elongate shaft 110. In some embodiments, the surgical anchor delivery device 100 may comprise a handle 140 including an actuation mechanism 150. In some embodiments, the elongate shaft 110 may extend distally away from the handle 140 to the distal end 112. In some embodiments, the handle 140 may include a handle housing 142. In some embodiments, the handle housing 142 may comprise a first housing member and a second housing member designed to mate with one another, in a "clam shell" configuration, for example. Other configurations are also contemplated.

In some embodiments, the handle 140 may be coupled to the elongate shaft 110. In some embodiments, the elongate shaft 110 may be axially and/or rotationally secured relative to the handle 140. In some embodiments, the elongate shaft 110 may be fixedly attached to the handle 140. The elongate shaft 110 may include a wall defining an outer surface and the lumen 120 extending therein. In some embodiments, the distal end 112 of the elongate shaft 110 may include a distal face 114, as seen in FIG. 4. In some embodiments, the distal face 114 may be oriented substantially perpendicular to a central longitudinal axis of the elongate shaft 110.

In some embodiments, the elongate shaft 110 may include at least one tine 116 extending distally away from the distal end 112 and/or the distal face 114 of the elongate shaft 110. In at least some embodiments, the at least one tine 116 may extend parallel to the central longitudinal axis of the elongate shaft 110. In some embodiments, the at least one tine 116 may include exactly one tine, or the at least one tine 116 may include two tines, three tines, four tines, or more tines as needed or desired.

Collectively, the at least one tine 116 may define and/or border a passage through which a surgical anchor (not shown in FIG. 4) may pass through as the surgical anchor is advanced and/or deployed out of the elongate shaft 110. Further, the at least one tine 116 may be designed to create a pilot hole at the treatment site (e.g., within tissue and/or the implant 12). For example, after a user positions and/or aligns the distal end 112 of the elongate shaft 110 along the implant 12, the user may apply a force to the handle 140 and/or the elongate shaft 110 such that the at least one tine 116 pierces through the implant 12 and/or into tissue at the treatment site (e.g., the distal tendon 24), thereby creating a pilot hole for which a portion of a surgical anchor may be inserted.

In some embodiments, the at least one tine 116 may include at least one curved side (e.g., a concave surface facing a second opposed tine of the at least one tine 116) and a pointed end or tip. In some examples, a curved side of the at least one tine 116 may be configured to mate with and/or correspond to a portion of the surgical anchor in a complimentary manner. In some embodiments, the at least one tine 116 may take various shapes, such as spikes, spears, prongs, or other shapes. The at least one tine 116 may generally have a pointed distal end or tip for piercing tissue or bone.

In some embodiments, the surgical anchor delivery device 100 and/or the actuation mechanism 150 may comprise a trigger 152. In some embodiments, the trigger 152 may be and/or may include a lever, a knob, a button, a slider, etc. In some embodiments, the trigger 152 may be movable relative to the handle 140 and/or the handle housing 142 to activate, operate, and/or actuate the actuation mechanism 150. In some embodiments, the trigger 152 may be secured to the handle 140 and/or the handle housing 142. In some embodiments, the trigger 152 may be secured to and/or pivotable relative to the handle 140 and/or the handle housing 142 at a pivot point 154, as seen in FIG. 3. Other configurations, while not expressly shown, are also contemplated. For example, in some embodiments, the trigger 152 may be secured to and/or slidable relative to the handle 140 and/or the handle housing 142. In some embodiments, the trigger 152 may be secured to and/or movable inward relative to the handle 140 and/or the handle housing 142 (e.g., toward an interior of the handle 140 and/or the handle housing 142). In some embodiments, the trigger 152 may be a touch sensitive structure. Other configurations are also contemplated. It can be appreciated that the handle 140 may be designed such that a user may grasp the handle 140 and/or the handle housing 142 with one hand and actuate and/or depress the trigger 152 with that same hand (e.g., via squeezing, etc.).

In some embodiments, the actuation mechanism 150 may be disposed within an interior of the surgical anchor delivery device 100, the handle 140, the handle housing 142, and/or the elongate shaft 110. In some embodiments, at least a portion of the trigger 152 may be disposed within the interior of the surgical anchor delivery device 100, the handle 140, and/or the handle housing 142. At least some additional details pertaining to the actuation mechanism 150 will be described below.

In some embodiments, the surgical anchor delivery device 100 may comprise a plurality of surgical anchors 200 (e.g., FIG. 5-6) or a plurality of surgical anchors 300 (e.g., FIGS.

6, 9) disposed within the lumen 120 of the elongate shaft 110. The surgical anchors will be discussed in more detail herein, but it will be appreciated that features and/or characteristics of the surgical anchors may be combined and/or applied interchangeably between various configurations of the surgical anchors. Further, it shall be understood that the surgical anchor delivery device 100 may be compatible with and/or may be used with any and/or all surgical anchors disclosed and/or described herein, as well as others. One beneficial aspect of the disclosure is that the plurality of surgical anchors 200 or the plurality of surgical anchors 300 may be disposed within the elongate shaft 110 prior to advancing the distal end 112 of the elongate shaft 110 to the treatment site. Accordingly, loading and/or reloading individual surgical anchors during a procedure may be avoided.

Figure 5:
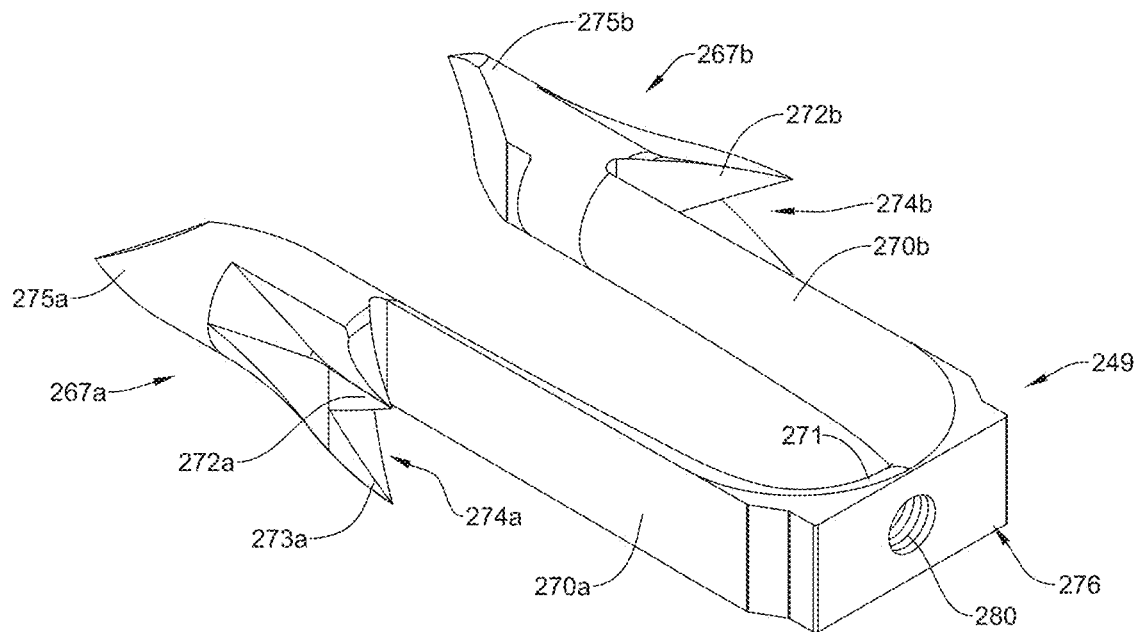
FIG. 5 illustrates selected aspects of a surgical anchor.

FIG. 5 illustrates selected aspects of one example configuration for a surgical anchor of the plurality of surgical anchors 200 which may be utilized with the surgical anchor delivery device 100 described herein. Although the various parts of the surgical anchor of the plurality of surgical anchors 200 are depicted in relative proportion to other parts of the surgical anchor of the plurality of surgical anchors 200, other configurations in size and orientation of the various parts are also contemplated.

In some embodiments, the surgical anchor of the plurality of surgical anchors 200 includes a first arm 270a, a second arm 270b, and a bridge 271 extending between the first arm 270a and the second arm 270b. In some embodiments, the bridge 271 may extend transversely relative to the first arm 270a and/or the second arm 270b. In at least some embodiments, the bridge 271 may extend from and/or adjacent to a proximal end of the first arm 270a to a proximal end of the second arm 270b. In some embodiments, the bridge 271 may abut the proximal end of the first arm 270a and the proximal end of the second arm 270b. In some embodiments, the bridge 271 may be integrally formed with and/or may be monolithically formed with the first arm 270a and/or the second arm 270b.

In some embodiments, the first arm 270a may include a first anchor portion 267a and the second arm 270b may include a second anchor portion 267b. In some embodiments, the first anchor portion 267a may include a first projection 272a and a second projection 273a extending outwardly therefrom. The first anchor portion 267a, the first projection 272a, and/or the second projection 273a may be configured to engage with tissue (e.g., the distal tendon 24, etc.). In some embodiments, the second anchor portion 267b may include a first projection 272b and a second projection (not shown, but similar to the first projection 272b and/or the second projection 273a) extending outwardly therefrom. The second anchor portion 267b, the first projection 272b, and/or the second projection (not shown) may be configured to engage with tissue (e.g., the distal tendon 24, etc.). In some embodiments, the first projection 272a and the second projection 273a of the first anchor portion 267a may define a first notch 274a positioned between the first projection 272a and the second projection 273a of the first anchor portion 267a. In some embodiments, the first projection 272b and the second projection (not shown) of the second anchor portion 267b may define a second notch 274b positioned between the first projection 272b and the second projection (not shown) of the second anchor portion 267b. In some embodiments, a distal end region of the first anchor portion 267a may include a sharp and/or pointed end 275a configured to pierce and/or to aid in piercing though the implant 12 and/or tissue (e.g., the distal tendon 24). In some embodiments, a distal end region of the second anchor portion 267b may include a sharp and/or pointed end 275b configured to pierce and/or to aid in piercing though the implant 12 and/or tissue (e.g., the distal tendon 24). Other configurations for the surgical anchor of the plurality of surgical anchors 200, the first anchor portion 267a, and/or the second anchor portion 267b are also contemplated.

In some embodiments, a proximal end 249 of the surgical anchor of the plurality of surgical anchors 200 may include a flat surface 276 positioned along a proximal side of the bridge 271 and/or facing proximally. In some embodiments, the flat surface 276 may be a planar surface arranged generally perpendicular to the central longitudinal axis of the elongate shaft 110 of the surgical anchor delivery device 100 when loaded therein. The bridge 271 may include a threaded aperture 280 disposed therein and/or extending therethrough. In some embodiments, the threaded aperture 280 may be oriented generally parallel to the central longitudinal axis of the elongate shaft 110 when the surgical anchor of the plurality of surgical anchors 200 is disposed within the elongate shaft 110 and/or the lumen 120. In some embodiments, the threaded aperture 280 may be coaxial and/or coincident with the central longitudinal axis of the elongate shaft 110 when the surgical anchor of the plurality of surgical anchors 200 is disposed within the elongate shaft 110 and/or the lumen 120. In some embodiments, the threaded aperture 280 may cooperate with the actuation mechanism 150 to advance the surgical anchor of the plurality of surgical anchors 200 toward the distal end 112 of the elongate shaft 110 and/or out of the lumen 120 as discussed herein.

Figure 6:
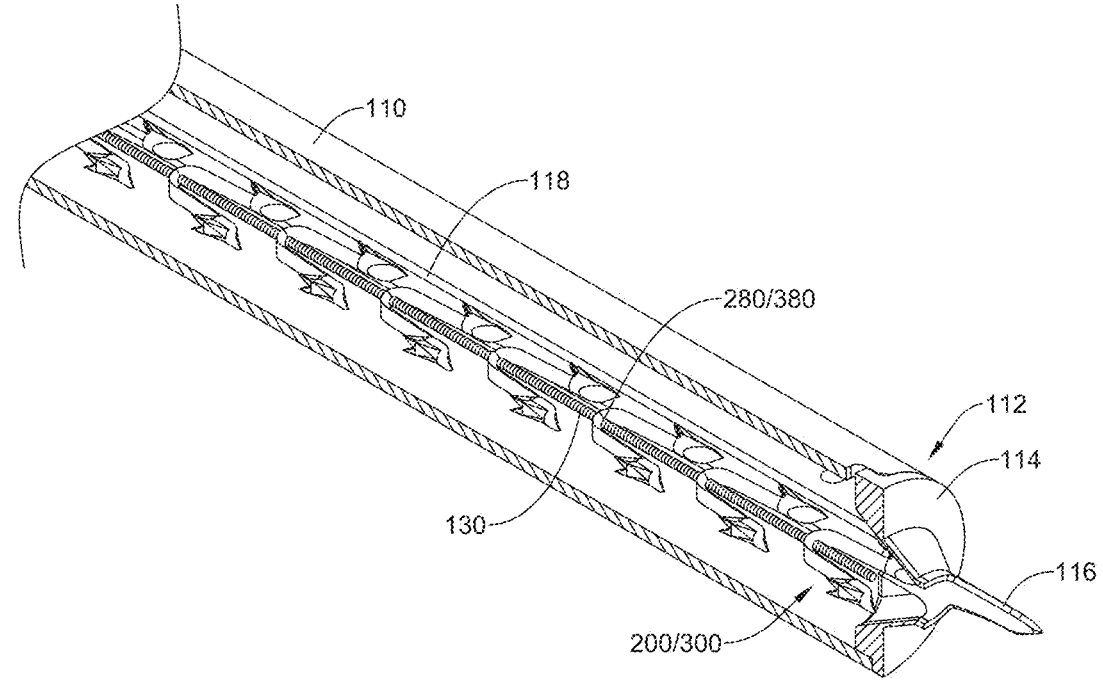
FIG. 6 is a partial cross-sectional view illustrating selected aspects of the surgical anchor delivery device.

FIG. 6 is a partial cross-sectional view illustrating selected aspects of the surgical anchor delivery device 100. As seen in FIG. 6, the elongate shaft 110 may include the plurality of surgical anchors 200 or the plurality of surgical anchors 300 disposed and/or positioned within the lumen 120 of the elongate shaft 110. Additionally, at least a portion of the actuation mechanism 150 (e.g., FIG. 3, FIG. 11) may extend into the elongate shaft 110 and/or the lumen 120 of the elongate shaft 110. In at least some embodiments, the surgical anchor delivery device 100 and/or the actuation mechanism 150 (e.g., FIG. 3, FIG. 11) may include a threaded rod 130 disposed within and/or extending within the elongate shaft 110 and/or the lumen 120 of the elongate shaft 110. The threaded rod 130 may be configured to threadably engage with the plurality of surgical anchors 200 or the plurality of surgical anchors 300. In some embodiments, the threaded rod 130 may be configured to threadably engage with the threaded aperture 280 of the surgical anchor of the plurality of surgical anchors 200 (e.g., FIG. 5-8) or a threaded aperture 380 (e.g., FIGS. 6, 9) of a surgical anchor of the plurality of surgical anchors 300.

In the interest of brevity, FIGS. 6-8 will be described with respect to the plurality of surgical anchors 200. However, it shall be understood that the plurality of surgical anchors 300 may be used in place of the plurality of surgical anchors 200 with little or no change to the surgical anchor delivery device 100.

As seen in FIG. 6, the plurality of surgical anchors 200 may be oriented in longitudinal alignment with the central longitudinal axis of the elongate shaft 110 with the sharp and/or pointed ends 275a/275b of the plurality of surgical anchors 200 pointed toward the distal end 112 of the elongate shaft 110.

In some embodiments, the plurality of surgical anchors 200 may be spaced away from one another along the central longitudinal axis of the elongate shaft 110 and/or within the lumen 120 of the elongate shaft 110 such that adjacent surgical anchors of the plurality of surgical anchors 200 do not directly contact one another. It can be appreciated from FIG. 6 that the plurality of surgical anchors 200 may be spaced apart from one another while threaded onto the threaded rod 130. As such, the surgical anchor delivery device 100 may be initially loaded with the plurality of surgical anchors 200, such as two or more surgical anchors, three or more surgical anchors, four or more surgical anchors, six or more surgical anchors, eight or more surgical anchors, etc. for sequential deployment from the surgical anchor delivery device 100 and/or the distal end 112 of the elongate shaft 110. As discussed herein, the plurality of surgical anchors 200 may be sequentially advanced out of the distal end 112 of the elongate shaft 110 as the actuation mechanism 150 is manipulated and/or actuated, such as via the handle 140 and/or the trigger 152 (e.g., FIG. 3).

In some embodiments, rotation of the threaded rod 130 within and/or relative to the elongate shaft 110 may advance the plurality of surgical anchors 200 within the lumen 120 toward the distal end 112 of the elongate shaft 110. In some embodiments, rotation of the threaded rod 130 within and/or relative to the elongate shaft 110 may advance the plurality of surgical anchors 200 within the lumen 120 toward the distal end 112 of the elongate shaft 110 without rotating the plurality of surgical anchors 200 within the lumen 120 and/or relative to the elongate shaft 110. In some embodiments, the plurality of surgical anchors 200 may be prevented from rotating relative to the elongate shaft 110. In at least some embodiments, rotation of the threaded rod 130 within and/or relative to the elongate shaft 110 may be configured to advance the plurality of surgical anchors 200 out of the lumen 120 and/or the distal end 112 of the elongate shaft 110. In some embodiments, the plurality of surgical anchors 200 may be configured to slide distally within the lumen 120 and/or the elongate shaft 110 in response to rotation of the threaded rod 130 within and/or relative to the elongate shaft 110.

In some embodiments, rotation of the threaded rod 130 within and/or relative to the elongate shaft 110 may be configured to drive at least one barb (e.g., the first anchor portion 267a and/or the second anchor portion 267b, etc.) extending distally from the bridge 271 of each surgical anchor of the plurality of surgical anchors 200 into the implant 12 and/or a target tissue (e.g., the distal tendon 24), as seen schematically in FIGS. 1-2.

Returning to FIGS. 6 and 7, in some embodiments, the elongate shaft 110 may include a channel 118 extending longitudinally along a wall of the elongate shaft 110 and opening radially inwards. In some embodiments, the elongate shaft 110 may include a second channel extending longitudinally along the wall of the elongate shaft 110 and opening radially inwards. The second channel may be disposed opposite the channel 118 and/or on an opposite side of the lumen 120 with respect to the central longitudinal axis of the elongate shaft 110.

In some embodiments, the channel 118 and/or the second channel may be formed separately from the elongate shaft 110 and fixedly attached to the elongate shaft 110 along an inner surface of the wall of the elongate shaft 110. In some embodiments, the channel 118 and/or the second channel may be fixedly attached to the elongate shaft 110 with adhesives, welding, mechanical fasteners, friction or interference fit, etc. In some embodiments, the channel 118 and/or the second channel may be integrally formed with and/or may be monolithically formed with the wall of the elongate shaft 110. In some embodiments, the channel 118 and/or the second channel may be formed in the wall of the elongate shaft 110. In some embodiments, the channel 118 and/or the second channel may be extruded, injection molded, machined, etc. with the elongate shaft 110. Other methods of manufacturing and/or assembly are also contemplated.

Figure 7:
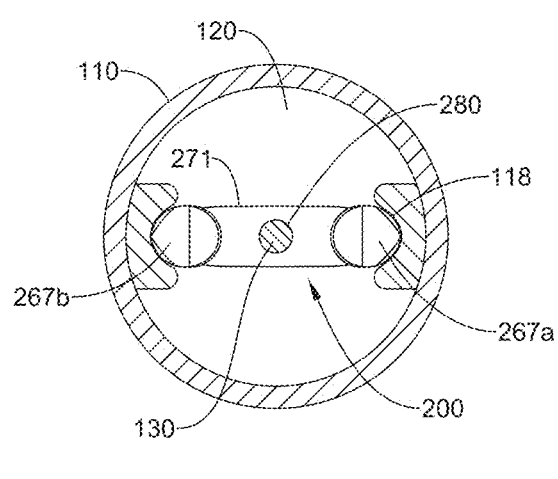
FIG. 7 is a partial cross-sectional view illustrating selected aspects of a configuration of the surgical anchor delivery device.

As seen in FIGS. 6 and 7, the first anchor portion 267a and/or the second anchor portion 267b may be disposed adjacent to and/or within the channel 118 and/or the second channel. In some embodiments, the channel 118 and/or the second channel may be configured to prevent rotation of the plurality of surgical anchors 200 within the lumen 120 and/or relative to the elongate shaft 110.

Figure 8:
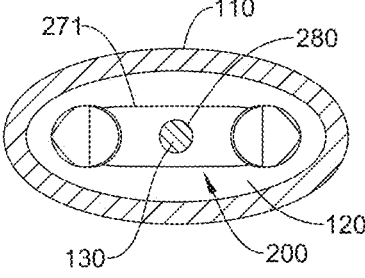
FIG. 8 is a partial cross-sectional view illustrating selected aspects of an alternative configuration of the surgical anchor delivery device.

In an alternative configuration shown in FIG. 8, in some embodiments, the lumen 120 and/or the elongate shaft 110 may include and/or may have a noncircular cross-sectional shape. In some embodiments, each surgical anchor of the plurality of surgical anchors 200 may include and/or may have a noncircular perimeter shape. In at least some embodiments, the noncircular perimeter shape of the plurality of surgical anchors 200 may cooperate with the noncircular cross-sectional shape of the lumen 120 and/or the elongate shaft 110 to prevent the plurality of surgical anchors 200 from rotating relative to the elongate shaft 110.

Figure 9:
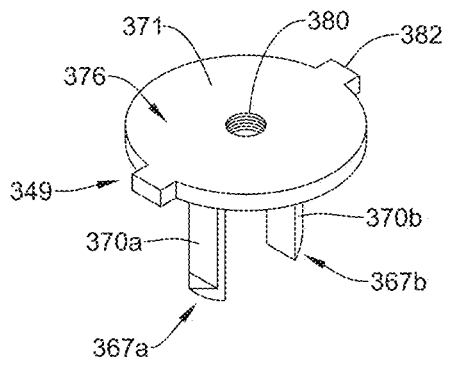
FIG. 9 illustrates selected aspects of a surgical anchor.

FIG. 9 illustrates selected aspects of one example configuration for a surgical anchor of the plurality of surgical anchors 300 which may be utilized with the surgical anchor delivery device 100 described herein. Although the various parts of the surgical anchor of the plurality of surgical anchors 300 are depicted in relative proportion to other parts of the surgical anchor of the plurality of surgical anchors 300, other configurations in size and orientation of the various parts are also contemplated.

In some embodiments, the surgical anchor of the plurality of surgical anchors 300 includes a first arm 370a, a second arm 370b, and a bridge 371 extending between the first arm 370a and the second arm 370b. In some embodiments, the bridge 371 may extend transversely relative to the first arm 370a and/or the second arm 370b. In at least some embodiments, the bridge 371 may extend from and/or adjacent to a proximal end of the first arm 370a to a proximal end of the second arm 370b. In some embodiments, the bridge 371 may abut the proximal end of the first arm 370a and the proximal end of the second arm 370b. In some embodiments, the bridge 371 may be integrally formed with and/or may be monolithically formed with the first arm 370a and/or the second arm 370b. In some embodiments, the bridge 371 may include a substantially rounded and/or circular perimeter shape. Other configurations are also contemplated.

In some embodiments, the first arm 370a may include a first anchor portion 367a and the second arm 370b may include a second anchor portion 367b. In some embodiments, the first anchor portion 367a and the second anchor portion 367b may include features from and/or may be similar to the first anchor portion 267a and the second anchor portion 267b, respectively. For example, in some embodiments, the first anchor portion 367a may include a first projection and a second projection extending outwardly therefrom. The first anchor portion 367a, the first projection, and/or the second projection may be configured to engage with tissue (e.g., the distal tendon 24, etc.). In some embodiments, the second anchor portion 367b may include a first projection and a second projection extending outwardly therefrom. The second anchor portion 367b, the first projection, and/or the second projection may be configured to engage with tissue (e.g., the distal tendon 24, etc.).

In some embodiments, a distal end region of the first anchor portion 367a may include a sharp and/or pointed end configured to pierce and/or to aid in piercing though the implant 12 and/or tissue (e.g., the distal tendon 24). In some embodiments, a distal end region of the second anchor portion 367b may include a sharp and/or pointed end configured to pierce and/or to aid in piercing though the implant 12 and/or tissue (e.g., the distal tendon 24). Other configurations for the surgical anchor of the plurality of surgical anchors 300, the first anchor portion 367a, and/or the second anchor portion 367b are also contemplated.

In some embodiments, a proximal end 349 of the surgical anchor of the plurality of surgical anchors 300 may include a flat surface 376 positioned along a proximal side of the bridge 371 and/or facing proximally. In some embodiments, the flat surface 376 may be a planar surface arranged generally perpendicular to the central longitudinal axis of the elongate shaft 110 of the surgical anchor delivery device 100 when loaded therein. In some embodiments, each surgical anchor of the plurality of surgical anchors 300 may include a tab 382 extending radially outward from a peripheral edge of the surgical anchor and/or the bridge 371.

The bridge 371 may include a threaded aperture 380 disposed therein and/or extending therethrough. In some embodiments, the threaded aperture 380 may be oriented generally parallel to the central longitudinal axis of the elongate shaft 110 when the surgical anchor of the plurality of surgical anchors 300 is disposed within the elongate shaft 110 and/or the lumen 120. In some embodiments, the threaded aperture 380 may be coaxial and/or coincident with the central longitudinal axis of the elongate shaft 110 when the surgical anchor of the plurality of surgical anchors 300 is disposed within the elongate shaft 110 and/or the lumen 120. In some embodiments, the threaded aperture 380 may cooperate with the actuation mechanism 150 to advance the surgical anchor of the plurality of surgical anchors 300 toward the distal end 112 of the elongate shaft 110 and/or out of the lumen 120 as discussed herein.

Figure 10:
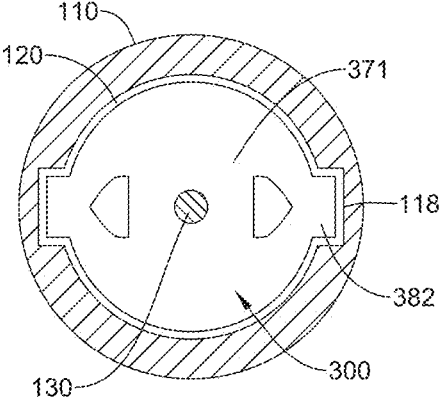
FIG. 10 is a partial cross-sectional view illustrating selected aspects of a configuration of the surgical anchor delivery device.

FIG. 10 is a partial cross-sectional view illustrating selected aspects of an alternative configuration of the surgical anchor delivery device 100 and/or the elongate shaft 110 of FIG. 6. The threaded rod 130 may be configured to threadably engage with the plurality of surgical anchors 300. In some embodiments, the threaded rod 130 may be configured to threadably engage with the threaded aperture 380 of a surgical anchor of the plurality of surgical anchors 300.

Similar to the configuration seen in FIG. 6, the plurality of surgical anchors 300 may be oriented in longitudinal alignment with the central longitudinal axis of the elongate shaft 110 with the sharp and/or pointed ends of the plurality of surgical anchors 300 pointed toward the distal end 112 of the elongate shaft 110.

In some embodiments, the plurality of surgical anchors 300 may be spaced away from one another along the central longitudinal axis of the elongate shaft 110 and/or within the lumen 120 of the elongate shaft 110 such that adjacent surgical anchors of the plurality of surgical anchors 300 do not directly contact one another. It can be appreciated that the plurality of surgical anchors 300 may be spaced apart from one another while threaded onto the threaded rod 130. As such, the surgical anchor delivery device 100 may be initially loaded with the plurality of surgical anchors 300, such as two or more surgical anchors, three or more surgical anchors, four or more surgical anchors, six or more surgical anchors, eight or more surgical anchors, etc. for sequential deployment from the surgical anchor delivery device 100 and/or the distal end 112 of the elongate shaft 110. As discussed herein, the plurality of surgical anchors 300 may be sequentially advanced out of the distal end 112 of the elongate shaft 110 as the actuation mechanism 150 is manipulated and/or actuated, such as via the handle 140 and/or the trigger 152 (e.g., FIG. 3).

In some embodiments, rotation of the threaded rod 130 within and/or relative to the elongate shaft 110 may advance the plurality of surgical anchors 300 within the lumen 120 toward the distal end 112 of the elongate shaft 110. In some embodiments, rotation of the threaded rod 130 within and/or relative to the elongate shaft 110 may advance the plurality of surgical anchors 300 within the lumen 120 toward the distal end 112 of the elongate shaft 110 without rotating the plurality of surgical anchors 300 within the lumen 120 and/or relative to the elongate shaft 110. In some embodiments, the plurality of surgical anchors 300 may be prevented from rotating relative to the elongate shaft 110.

In at least some embodiments, rotation of the threaded rod 130 within and/or relative to the elongate shaft 110 may be configured to advance the plurality of surgical anchors 300 out of the lumen 120 and/or the distal end 112 of the elongate shaft 110. In some embodiments, the plurality of surgical anchors 300 may be configured to slide distally within the lumen 120 and/or the elongate shaft 110 in response to rotation of the threaded rod 130 within and/or relative to the elongate shaft 110.

In some embodiments, rotation of the threaded rod 130 within and/or relative to the elongate shaft 110 may be configured to drive at least one barb (e.g., the first anchor portion 367a and/or the second anchor portion 367b, etc.) extending distally from the bridge 371 of each surgical anchor of the plurality of surgical anchors 300 into the implant 12 and/or a target tissue (e.g., the distal tendon 24), as seen schematically in FIGS. 1-2.

Returning to FIG. 10, in some embodiments, the elongate shaft 110 may include a channel 118 extending longitudinally along a wall of the elongate shaft 110 and opening radially inwards. In some embodiments, the elongate shaft 110 may include a second channel extending longitudinally along the wall of the elongate shaft 110 and opening radially inwards. The second channel may be disposed opposite the channel 118 and/or on an opposite side of the lumen 120 with respect to the central longitudinal axis of the elongate shaft 110.

In some embodiments, the channel 118 and/or the second channel may be formed along an inner surface of the wall of the elongate shaft 110. In some embodiments, the channel 118 and/or the second channel may be formed within the wall of the elongate shaft 110. In some embodiments, the channel 118 and/or the second channel may be integrally formed with and/or may be monolithically formed with the wall of the elongate shaft 110. In some embodiments, the channel 118 and/or the second channel may be extruded, injection molded, machined, etc. with the elongate shaft 110. Other methods of manufacturing and/or assembly are also contemplated.

As seen in FIG. 10, the tab 382 may be disposed adjacent to and/or within the channel 118 and/or the second channel. In some embodiments, the tab 382 may be configured to extend into the channel 118 and/or the second channel. In some embodiments, the channel 118 and/or the second channel may be configured to prevent rotation of the plurality of surgical anchors 300 within the lumen 120 and/or relative to the elongate shaft 110. In some embodiments, the tab 382 may cooperate with the channel 118 and/or the second channel to prevent rotation of the plurality of surgical anchors 300 within the lumen 120 and/or relative to the elongate shaft 110.

Figure 11:
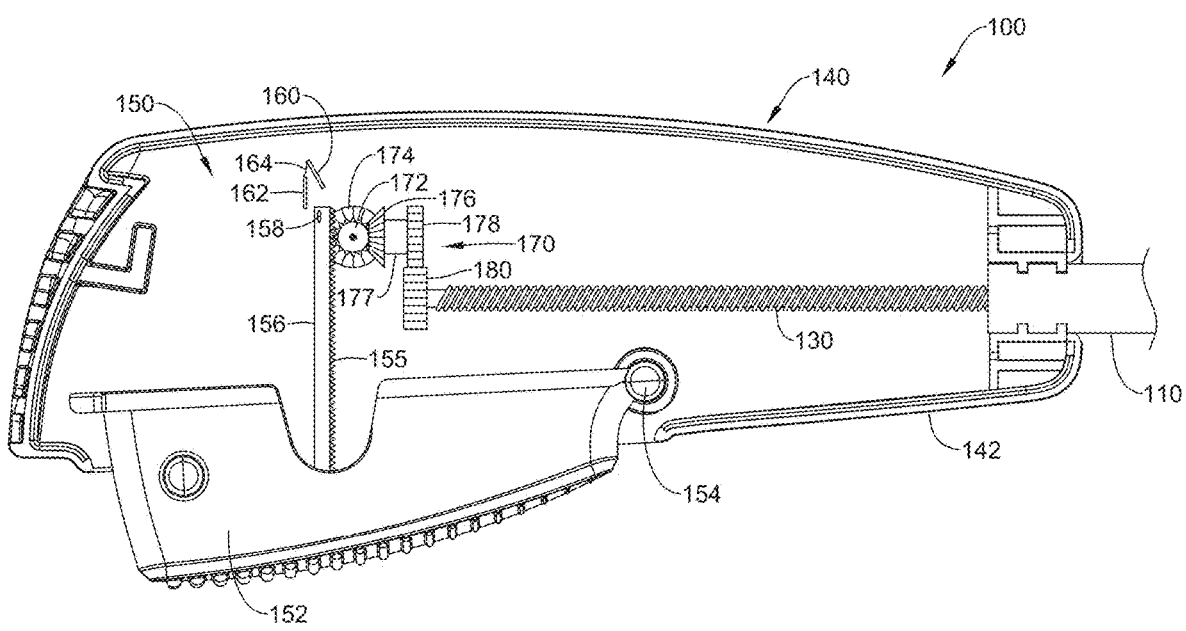
FIG. 11 illustrates selected aspects of the surgical anchor delivery device.

FIG. 11 schematically illustrates selected aspects of the surgical anchor delivery device 100 and/or the actuation mechanism 150. As shown, the elongate shaft 110 may extend from the handle 140 and/or the handle housing 142. The surgical anchor delivery device 100 and/or the handle 140 may include the actuation mechanism 150. In some embodiments, the surgical anchor delivery device 100 and/or the actuation mechanism 150 may include the trigger 152. In the example shown, the trigger 152 is pivotably coupled to the handle 140 and/or the handle housing 142. However, as discussed herein, the trigger 152 may take other forms and/or may be subject to other means of actuation. FIGS. 12-23 illustrate selected aspects related to the operation of the surgical anchor delivery device 100 and/or the actuation mechanism 150 and/or various embodiments and/or configurations thereof.

The actuation mechanism 150 may be configured to rotate the threaded rod 130 within and/or relative to the handle 140, the handle housing 142, and/or the elongate shaft 110 to advance the plurality of surgical anchors 200 or the plurality of surgical anchors 300 toward the distal end 112 (e.g., FIG. 3) of the elongate shaft 110. In at least some embodiments, the actuation mechanism 150 may be configured to rotate the threaded rod 130 in only a single direction. Accordingly, oscillation of the threaded rod 130 may be avoided, thereby ensuring that the plurality of surgical anchors 200 or the plurality of surgical anchors 300 is only advanced toward the distal end 112 of the elongate shaft 110 and the plurality of surgical anchors 200 or the plurality of surgical anchors 300 cannot be retracted or moved proximally within the lumen 120 and/or the elongate shaft 110.

In some embodiments, the actuation mechanism 150 may comprise a plurality of gears 170 disposed within the handle 140 and/or the handle housing 142. In some embodiments, the actuation mechanism 150 may comprise a rack 156 coupled to the trigger 152. In some embodiments, the rack 156 may be fixedly secured and/or fixedly attached to the trigger 152. In some embodiments, the rack 156 may be integrally formed with and/or may be monolithically formed with the trigger 152. The rack 156 may be an elongated structure having a plurality of teeth 155 extending from one side. In some embodiments, the plurality of teeth 155 may extend from a distally facing side of the rack 156, wherein the elongate shaft 110 extends distally from the handle 140 and/or the handle housing 142.

The rack 156 and/or the plurality of teeth 155 of the rack 156 may be configured to engage with the plurality of gears 170. In some embodiments, the plurality of gears 170 may comprise a pinion 172 configured to directly engage the rack 156 and/or the plurality of teeth 155 of the rack 156. In some embodiments, the plurality of gears 170 may comprise a first bevel gear 174 fixedly attached to the pinion 172. In some embodiments, the first bevel gear 174 may be fixedly attached to the pinion 172 by a first shaft (not visible). In the view shown in FIG. 11, the first bevel gear 174 is disposed below or underneath the pinion 172, and the first shaft would extend therebetween. In some embodiments, the plurality of gears 170 may comprise a second bevel gear 176 engaged with the first bevel gear 174 such that rotation of the pinion 172 and/or the first bevel gear 174 results in rotation of the second bevel gear 176. In some embodiments, the plurality of gears 170 may comprise a first spur gear 178 fixedly attached to the second bevel gear 176. In some embodiments, the first spur gear 178 may be fixedly attached to the second bevel gear 176 by a second shaft 177. In some embodiments, the plurality of gears 170 may comprise a second spur gear 180 fixedly attached to the threaded rod 130. In some embodiments, the second spur gear 180 may be disposed at a proximal end of the threaded rod 130.

In some embodiments, the rack 156 may include a projection 158 extending from the rack 156. In some embodiments, the projection 158 may extend from the rack 156 in a direction generally perpendicular to the plurality of teeth 155. In the view shown in FIG. 11, the projection 158 may extend upward out of the page or downward into the page.

In some embodiments, the handle 140, the handle housing 142, and/or the actuation mechanism 150 may include a first guide member 160 and a second guide member 162. The first guide member 160 and/or the second guide member 162 may be securely coupled to the handle 140 and/or the handle housing 142. In some embodiments, the first guide member 160 and/or the second guide member 162 may be fixedly attached to the handle 140 and/or the handle housing 142. In some embodiments, the first guide member 160 and/or the second guide member 162 may be integrally formed with and/or may be monolithically formed with the handle 140 and/or the handle housing 142. Other configurations are also contemplated.

In some embodiments, the first guide member 160 and/or the second guide member 162 may extend from and/or may be formed with the first housing member. In some embodiments, the first guide member 160 and/or the second guide member 162 may extend from and/or may be formed with the second housing member. In some embodiments, the first guide member 160 and/or the second guide member 162 may extend from and/or may be formed with the first housing member and the second housing member. Other configurations are also contemplated.

In some embodiments, the handle 140, the handle housing 142, and/or the actuation mechanism 150 may include a leaf spring 164 having a first end fixedly attached to the second guide member 162. In some embodiments, the first end of the leaf spring 164 may be fixedly attached to the second guide member 162 at and/or adjacent to a first end of the second guide member 162. The leaf spring 164 may extend from the first end thereof and/or from the first end of the second guide member 162 toward the first guide member 160. In some embodiments, a second end of the leaf spring 164 may engage with and/or may contact the first guide member 160. In some embodiments, the second end of the leaf spring 164 may be biased toward the first guide member 160. In some embodiments, the second end of the leaf spring 164 may be self-biased toward the first guide member 160. In some embodiments, the leaf spring 164 may be self-biased toward a straightened configuration. The second end of the leaf spring 164 may be engaged with the first guide member 160 such that the leaf spring 164 is held in a deflected configuration. Accordingly, the second end of the leaf spring 164 may be continuously and/or permanently biased toward the first guide member 160. However, the second end of the leaf spring 164 is not fixedly attached to the first guide member 160. Instead, the second end of the leaf spring 164 may be deflected away from the first guide member 160 when a force is applied to a distally facing surface of the leaf spring 164. Other configurations are also contemplated.

FIGS. 12-23 illustrate selected aspects related to the operation of the surgical anchor delivery device 100 and/or the actuation mechanism 150 and/or various embodiments and/or configurations thereof. It should be noted that not all features are shown and the illustrated aspects are shown in a highly schematic manner for ease of illustration and understanding.

Figure 12:
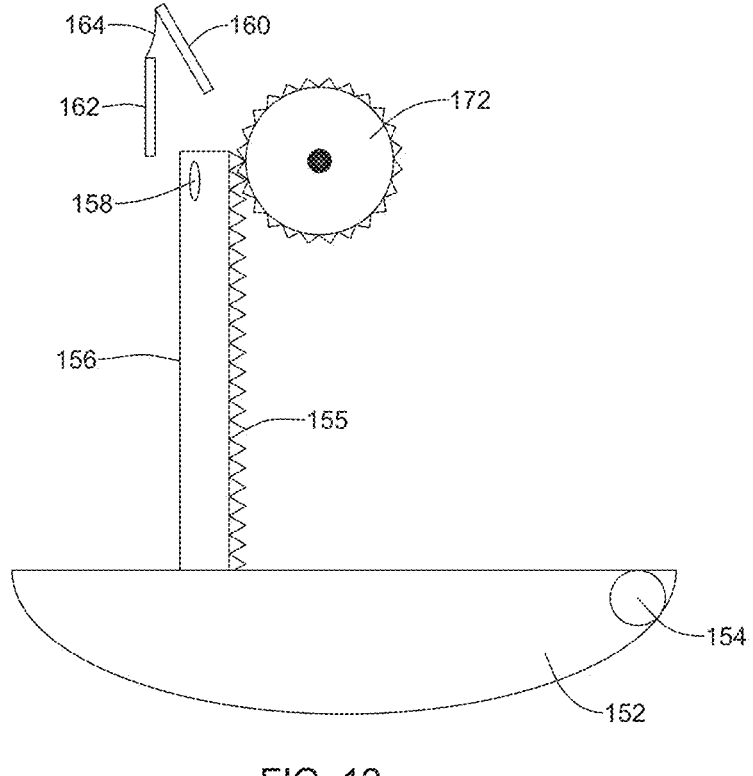
FIGS. 12-17 illustrate selected aspects of an actuation mechanism of the surgical anchor delivery device.

FIG. 12 shows the trigger 152 and the pivot point 154 where the trigger 152 is coupled to the handle 140 and/or the handle housing 142 (not shown). The rack 156 extends away from the trigger 152 and includes the plurality of teeth 155 extending in a distal direction. Other configurations are also contemplated. The projection 158 is shown extending out of the page from the rack 156. As discussed herein, this arrangement is not absolute, and in some embodiments, the projection 158 may extend in an opposite direction (e.g., into the page) from the rack 156. The first guide member 160 and the second guide member 162 may extend from the handle 140 and/or the handle housing 142. For example, the first guide member 160 and the second guide member 162 may extend inward from the first housing member and/or the second housing member. The first guide member 160 and the second guide member 162 may serve as guides for the projection 158 as the actuation mechanism 150 is actuated and/or operated.

Figure 14:
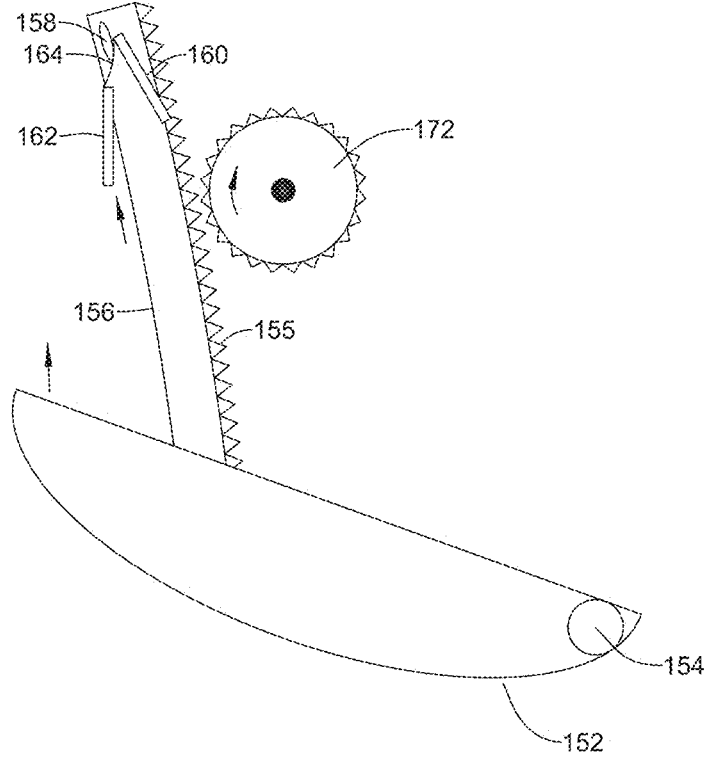
Figure 20:
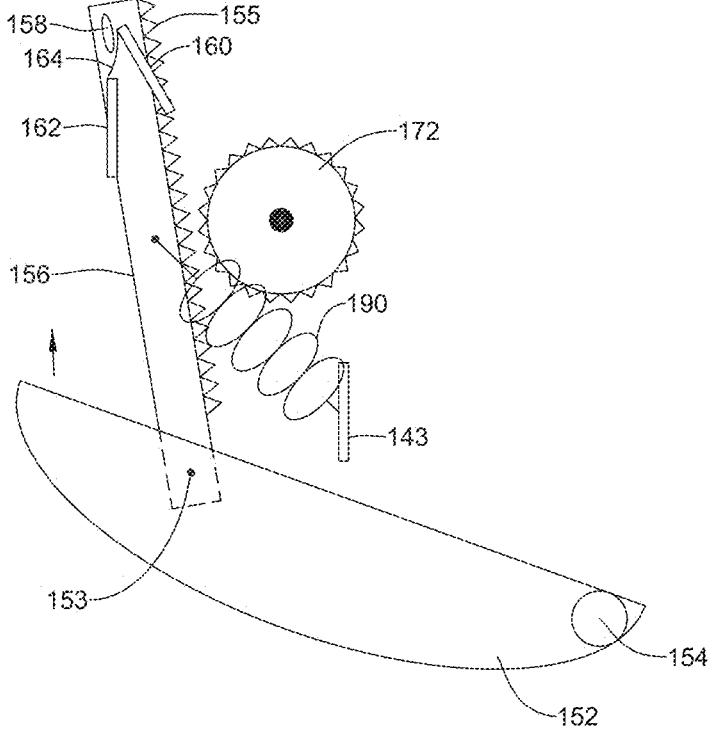

In some embodiments, the actuation mechanism 150 may be configured to shift between a starting position (e.g., FIGS. 11, 12, 18, 23) and an ending position (e.g., FIGS. 14, 20). In the starting position, the plurality of teeth 155 of the rack 156 may be engaged with the pinion 172 (e.g., teeth extending radially outward from the pinion 172).

Figure 13:
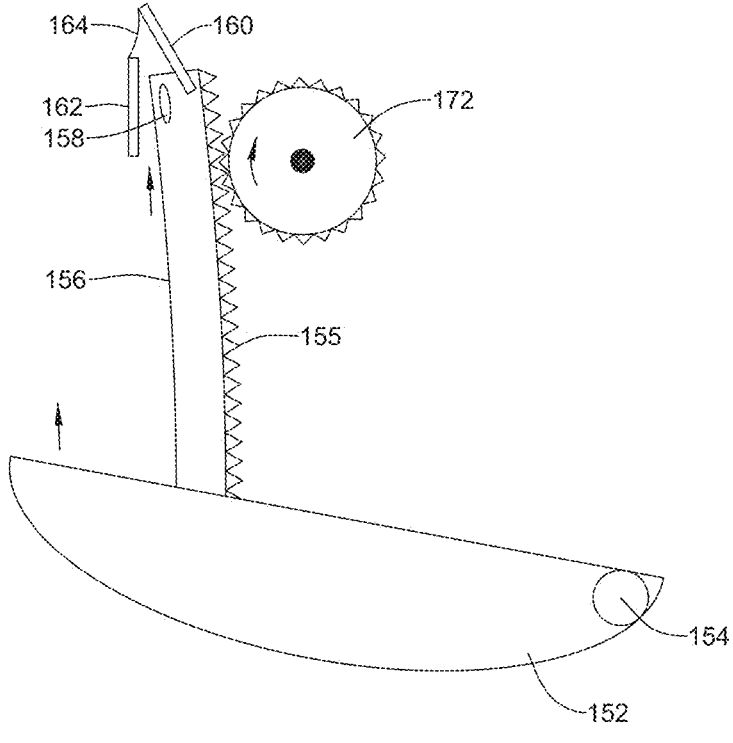

Actuating and/or activating the trigger 152 (e.g., squeezing the trigger 152, translating the trigger 152 toward the interior of the handle 140 and/or the handle housing 142, etc.) may translate the rack 156 along its length toward the ending position. As the rack 156 is translated within the handle 140 and/or the handle housing 142, the pinion 172 may be rotated by the plurality of teeth 155, as seen in FIG. 13. In some embodiments, the rack 156 may be semi-rigid and/or may deflect away from the pinion 172 as the rack 156 is translated relative to the pinion 172, as also seen in FIG. 13. This may result in an internal and/or inherent spring bias within the rack 156 that urges the rack 156 toward a straightened configuration. As such, the rack 156 may be self-biased toward the pinion 172, thereby keeping the plurality of teeth 155 engaged with the pinion 172. In some embodiments, actuation of the actuation mechanism 150 and/or translation of the rack 156 along and/or in engagement with the pinion 172 may rotate the threaded rod 130 (not shown) in a first direction. In some embodiments, the threaded rod 130 is only rotatable in the first direction.

At some point during translation of the rack 156 toward the ending position, but before reaching the ending position, the projection 158 may contact and/or engage the first guide member 160. The first guide member 160 may be angled away from the pinion 172. As such, as the projection 158 moves and/or translates along the first guide member 160, the rack 156 and/or the plurality of teeth 155 may be angled away from the pinion 172 and therefore the rack 156 and/or the plurality of teeth 155 may become less engaged with the pinion 172 until the rack 156 reaches the ending position, seen in FIG. 14. While translating the projection 158 along the first guide member 160, the projection 158 may contact and/or engage a distal side of the leaf spring 164. Prior to contacting the leaf spring 164, the projection 158 may be disposed distal of the leaf spring 164.

The leaf spring 164 may deflect and/or be urged away proximally from the first guide member 160 by the projection 158 until the protrusion moves past the leaf spring 164, at which time and/or point (e.g., the ending position) the leaf spring 164 may spring and/or snap back distally into position against the first guide member 160 with the projection 158 on an opposite side or a proximal side of the leaf spring 164, as seen in FIG. 14. After reaching the ending position, the rack 156 and/or the plurality of teeth 155 may be disengaged from the pinion 172.

In at least some embodiments, after reaching the ending position, the actuation mechanism 150 may be disengaged from the threaded rod 130 (not shown). Accordingly, after reaching the ending position, no further or additional rotation of the threaded rod 130 occurs until the actuation mechanism 150 has been reset to the starting position. Additionally, after reaching the ending position and/or after the actuation mechanism 150 disengages from the threaded rod 130, the actuation mechanism 150 may be configured to return to the starting position while disengaged from the threaded rod 130.

In some embodiments, a single actuation and/or a single activation of the actuation mechanism 150 may shift the actuation mechanism 150 from the starting position to the ending position. In at least some embodiments, shifting the actuation mechanism 150 from the starting position to the ending position may advance only one surgical anchor of the plurality of surgical anchors 200 or the plurality of surgical anchors 300 out of the lumen 120 and/or the distal end 112 of the elongate shaft 110.

Figure 15:
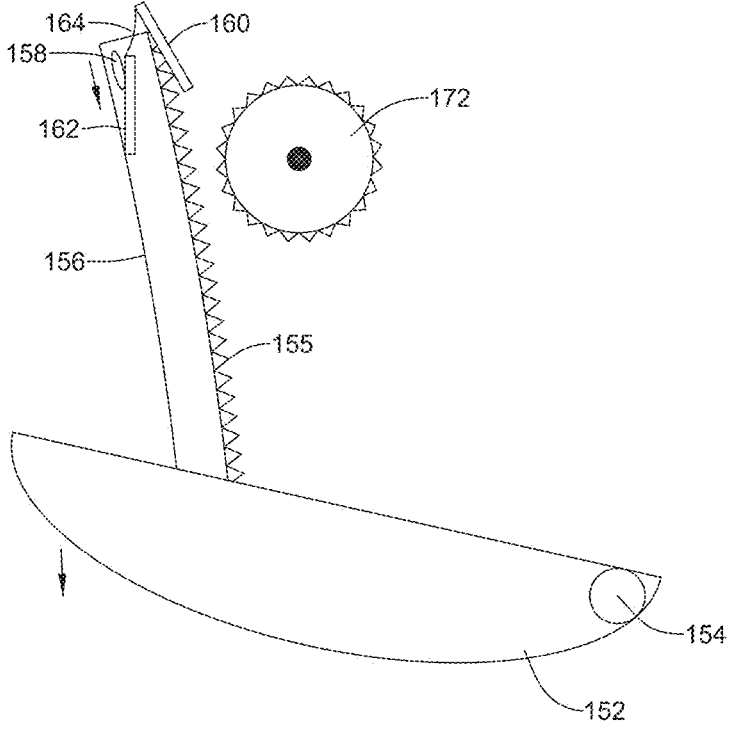
Figure 16:
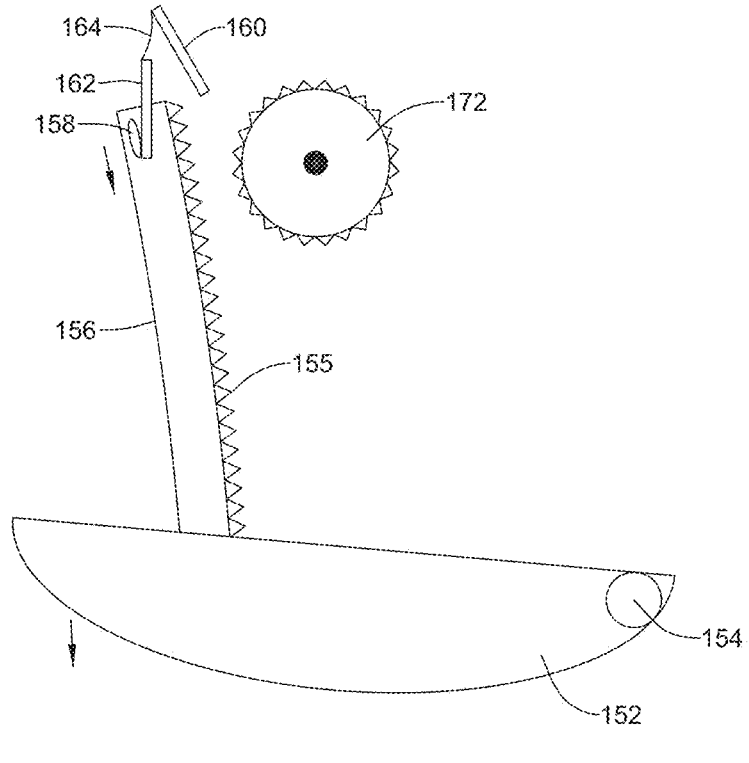

Returning and/or resetting the actuation mechanism 150 from the ending position to the starting position may include translating the trigger 152, the rack 156, and/or the projection 158 toward the starting position. Returning and/or resetting the actuation mechanism 150 from the ending position to the starting position may include translating the projection 158 along the opposite side or the proximal side of the leaf spring 164 toward the first end of the leaf spring 164, which may further direct the projection 158 toward and/or into engagement with the second guide member 162 and/or the first end of the second guide member 162. In some embodiments, the projection 158 may translate along a proximal facing surface of the second guide member 162 toward a second end of the second guide member 162 opposite the first end as the actuation mechanism 150 is returned and/or reset from the ending position toward the starting position, as seen in FIGS. 15-16. The second guide member 162 may cooperate with the projection 158 to prevent contact between the plurality of teeth 155 and the pinion 172 as the actuation mechanism 150 is returned and/or reset from the ending position toward the starting position. As such, the second guide member 162 may cooperate with the projection 158 to maintain the rack 156 disengaged from the pinion 172 and/or to maintain the actuation mechanism 150 disengaged from the threaded rod 130 as the actuation mechanism 150 is returned and/or reset from the ending position toward the starting position. In at least some embodiments, the threaded rod 130 does not rotate while resetting the actuation mechanism 150 toward and/or to the starting position.

In at least some embodiments, after reaching the ending position, the actuation mechanism 150 may be configured to automatically return to the starting position, thereby resetting the actuation mechanism 150 to advance another surgical anchor of the plurality of surgical anchors 200 or the plurality of surgical anchors 300 out of the lumen 120 and/or the distal end 112 of the elongate shaft 110 during a subsequent actuation and/or a subsequent activation of the actuation mechanism 150.

In some embodiments, the surgical anchor delivery device 100, the trigger 152, and/or the actuation mechanism 150 may be biased toward the starting position. In some embodiments, the trigger 152 and/or the actuation mechanism 150 may be self-biased toward the starting position. In some embodiments, the surgical anchor delivery device 100 and/ or the actuation mechanism 150 may include a spring engaged with the trigger 152 and/or the actuation mechanism 150. In one example, a torsion spring may be disposed within and/or in engagement with the trigger 152. The torsion spring may be engaged with the handle 140 and/or the handle housing 142 such that the torsion spring biases the trigger 152 toward the starting position. In another example, a coil spring may be disposed within the handle 140 and/or the handle housing 142, and the coil spring may be engaged with the trigger 152 to bias the trigger 152 and/or the actuation mechanism 150 toward the starting position. Other spring types and/or configurations, and/or other biasing elements, are also contemplated.

In some embodiments, the surgical anchor delivery device 100, the trigger 152, and/or the actuation mechanism 150 may include a ratcheting system or a locking system configured to prevent automatic return to the starting position prematurely. In some embodiments, as the trigger 152 and/or the actuation mechanism 150 is translated toward the ending position, the ratcheting system or the locking system may prevent reverse translation back toward the starting position. In some embodiments, the actuation mechanism 150 and/or the trigger 152 may only be translatable in a first direction (e.g., toward the ending position) until reaching the ending position and/or until the projection 158 is disposed on the proximal side of the leaf spring 164.

Figure 17:
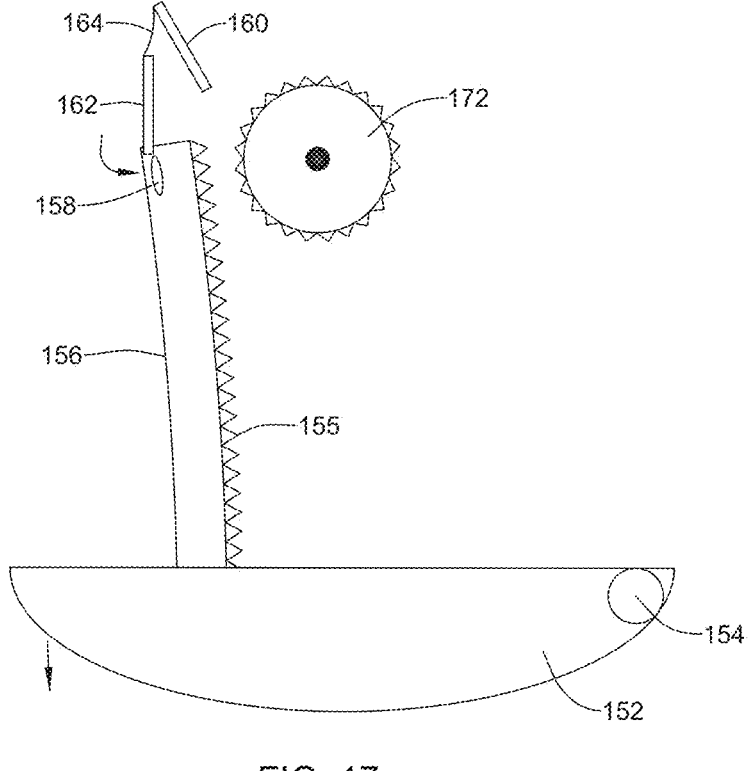

Once the projection 158 reaches and moves past the second end of the second guide member 162, the rack 156 may move and/or snap back toward the pinion 172 due to the internal and/or inherent spring bias in the rack 156, as seen in FIG. 17. The internal and/or inherent spring bias in the rack 156 urges the rack 156 back toward the straightened configuration and/or into engagement with the pinion 172 (e.g., back to the starting position). Once the rack 156 has returned to the starting position, thereby effectively resetting the actuation mechanism 150, the surgical anchor delivery device 100, the trigger 152, and/or the actuation mechanism 150 may then be cycled and/or activated again to advance another surgical anchor of the plurality of surgical anchors 200 or the plurality of surgical anchors 300 out of the lumen 120 and/or out the distal end 112 of the elongate shaft 110 and into the treatment site.

FIGS. 18-22 illustrate selected aspects of an alternative configuration of the actuation mechanism 150. The alternative configuration of FIGS. 18-22 may be structurally and/or functionally similar to the configurations of FIGS. 12-17, except where noted. In contrast to the configuration shown in FIGS. 11 and 12, in the alternative configuration of FIG. 18 the rack 156 is not fixedly attached to the trigger 152. Instead, the rack 156 is pivotably coupled to the trigger at a pivot point 153. In some embodiments, the pivot point 153 may be a pin, a hinge, or other similar structure. In further contrast the configuration shown in FIGS. 11 and 12, in the alternative configuration of FIG. 18 the rack 156 is substantially rigid and undergoes substantially no deflection as the rack 156 is translated. As a result of this difference, the rack 156 does not generate or include any internal and/or inherent spring bias urging the rack 156 back toward and/or into engagement with the pinion 172. Instead, the actuation mechanism 150 may include a tensioning spring 190 coupled to the rack 156. The tensioning spring 190 may be coupled to the rack 156 at a first end and coupled to the handle 140 and/or the handle housing 142 at a second end. For the purpose of illustration only, the handle 140 and/or the handle housing 142 are not shown completely, but a portion of the handle 140 and/or the handle housing 142 is illustrated as an anchoring or coupling point 143 for the tensioning spring 190.

Figure 18:
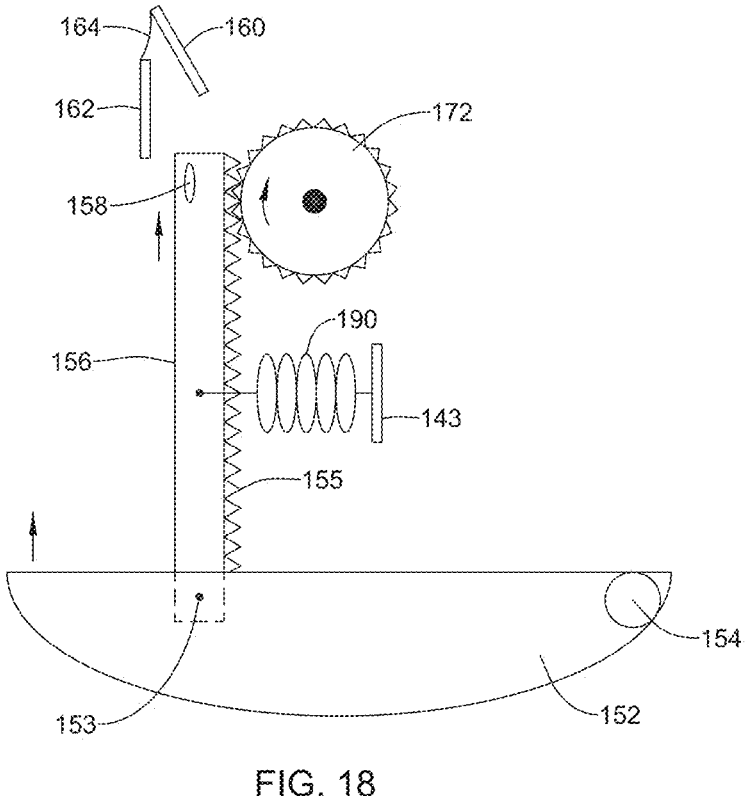
FIGS. 18-22 illustrate selected aspects of an actuation mechanism of the surgical anchor delivery device.

FIG. 18 shows the trigger 152 and the pivot point 154 where the trigger 152 is coupled to the handle 140 and/or the handle housing 142 (not shown). The rack 156 extends away from the trigger 152 and includes the plurality of teeth 155 extending in a distal direction. Other configurations are also contemplated. The projection 158 is shown extending out of the page from the rack 156. As discussed herein, this arrangement is not absolute, and in some embodiments, the projection 158 may extend in an opposite direction (e.g., into the page) from the rack 156. The first guide member 160 and the second guide member 162 may extend from the handle 140 and/or the handle housing 142. For example, the first guide member 160 and the second guide member 162 may extend inward from the first housing member and/or the second housing member. The first guide member 160 and the second guide member 162 may serve as guides for the projection 158 as the actuation mechanism 150 is actuated and/or operated.

In some embodiments, the actuation mechanism 150 may be configured to shift between a starting position (e.g., FIGS. 11, 18) and an ending position (e.g., FIG. 20). In the starting position, the plurality of teeth 155 of the rack 156 may be engaged with the pinion 172 (e.g., teeth extending radially outward from the pinion 172).

Figure 19:
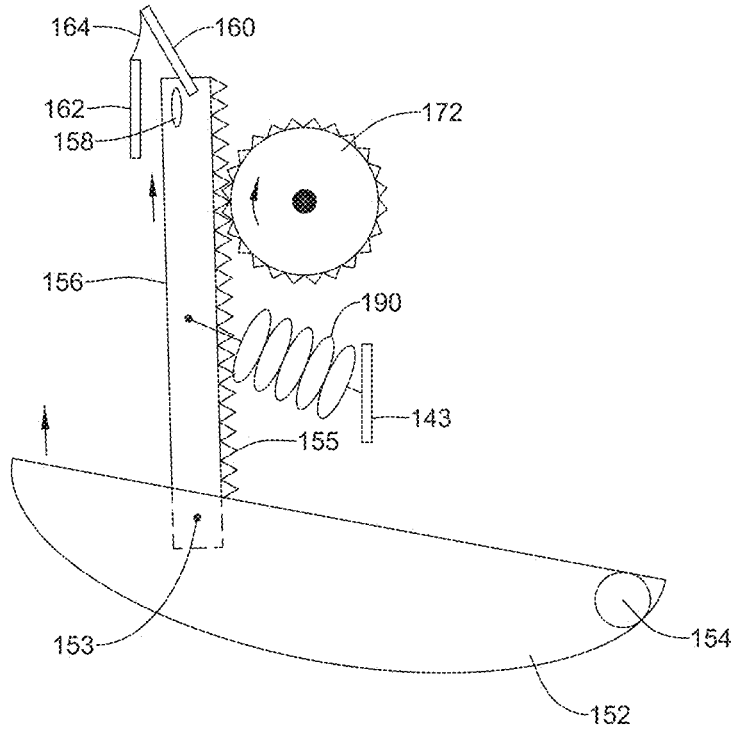

Actuating and/or activating the trigger 152 (e.g., squeezing the trigger 152, translating the trigger 152 toward the interior of the handle 140 and/or the handle housing 142, etc.) may translate the rack 156 along its length toward the ending position. As the rack 156 is translated within the handle 140 and/or the handle housing 142, the pinion 172 may be rotated by the plurality of teeth 155, as seen in FIGS. 18-19. In some embodiments, the rack 156 may be substantially rigid and/or may undergo substantially no deflection as the rack 156 is translated. In some embodiments, actuation of the actuation mechanism 150 and/or translation of the rack 156 along and/or in engagement with the pinion 172 may rotate the threaded rod 130 (not shown) in a first direction. In some embodiments, the threaded rod 130 is only rotatable in the first direction.

The tensioning spring 190 may be disposed on a distal side of the rack 156. The tensioning spring 190 may be held in tension. As such, the rack 156 may be biased toward the pinion 172, thereby keeping the plurality of teeth 155 engaged with the pinion 172. At some point during translation of the rack 156 toward the ending position, but before reaching the ending position, the projection 158 may contact and/or engage the first guide member 160. The first guide member 160 may be angled away from the pinion 172. As such, as the projection 158 moves and/or translates along the first guide member 160, the rack 156 and/or the plurality of teeth 155 may be angled away from the pinion 172 and therefore the rack 156 and/or the plurality of teeth 155 may become less engaged with the pinion 172 until the rack 156 reaches the ending position, seen in FIG. 20. As the rack 156 and/or the plurality of teeth 155 is angled away from the pinion 172 and the rack 156 and/or the plurality of teeth 155 become less engaged with the pinion 172, the tensioning spring 190 may stretch and/or tension on the tensioning spring 190 may increase, as seen in FIGS. 19-20. While translating the projection 158 along the first guide member 160, the projection 158 may contact and/or engage a distal side of the leaf spring 164. Prior to contacting the leaf spring 164, the projection 158 may be disposed distal of the leaf spring 164.

The leaf spring 164 may deflect and/or be urged away proximally from the first guide member 160 by the projection 158 until the protrusion moves past the leaf spring 164, at which time and/or point (e.g., the ending position) the leaf spring 164 may spring and/or snap back distally into position against the first guide member 160 with the projection 158 on an opposite side or a proximal side of the leaf spring 164, as seen in FIG. 20. After reaching the ending position, the rack 156 and/or the plurality of teeth 155 may be disengaged from the pinion 172.

In at least some embodiments, after reaching the ending position, the actuation mechanism 150 may be disengaged from the threaded rod 130 (not shown). Accordingly, after reaching the ending position, no further or additional rotation of the threaded rod 130 occurs until the actuation mechanism 150 has been reset to the starting position. Additionally, after reaching the ending position and/or after the actuation mechanism 150 disengages from the threaded rod 130, the actuation mechanism 150 may be configured to return to the starting position while disengaged from the threaded rod 130.

In some embodiments, a single actuation and/or a single activation of the actuation mechanism 150 may shift the actuation mechanism 150 from the starting position to the ending position. In at least some embodiments, shifting the actuation mechanism 150 from the starting position to the ending position may advance only one surgical anchor of the plurality of surgical anchors 200 or the plurality of surgical anchors 300 out of the lumen 120 and/or the distal end 112 of the elongate shaft 110.

Figure 21:
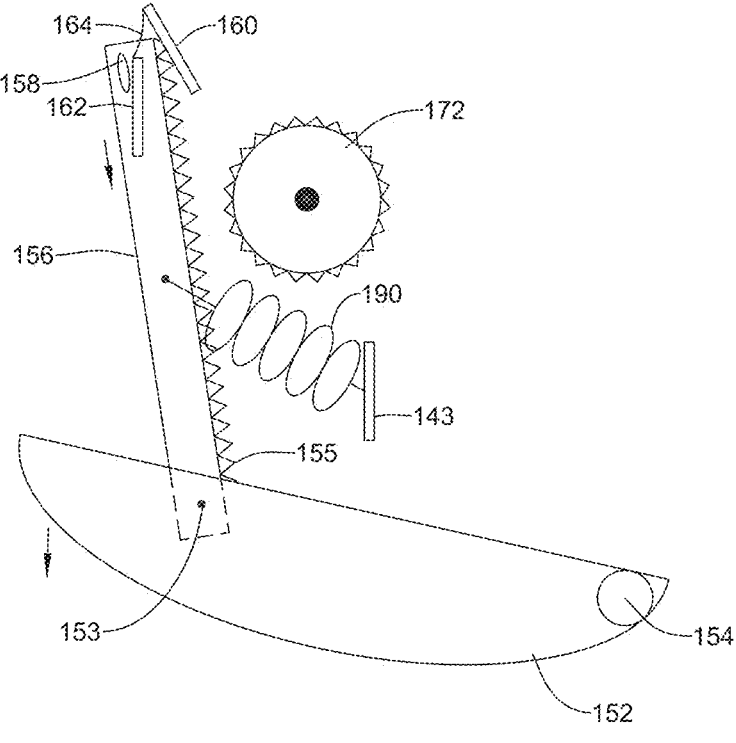
Figure 22:
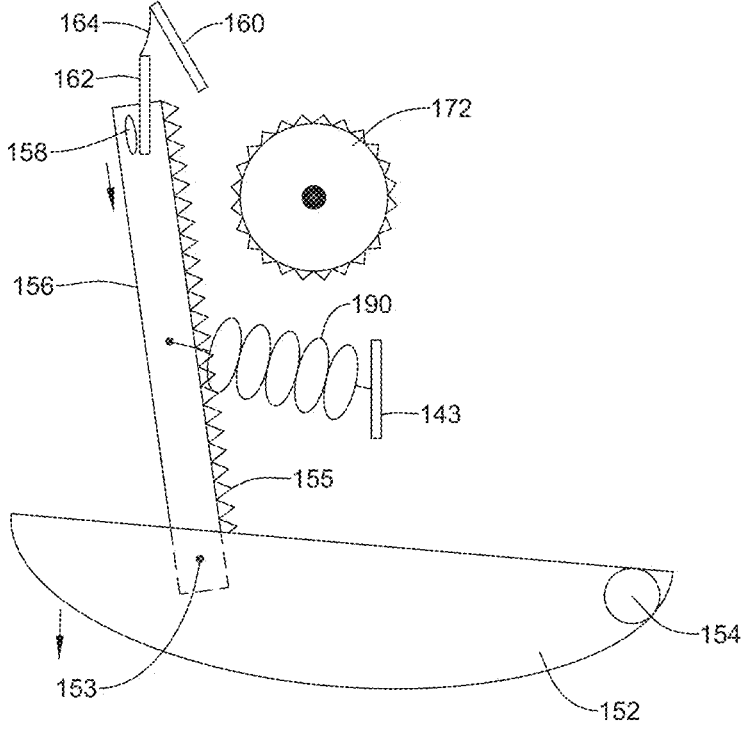

Returning and/or resetting the actuation mechanism 150 from the ending position to the starting position may include translating the trigger 152, the rack 156, and/or the projection 158 toward the starting position. Returning and/or resetting the actuation mechanism 150 from the ending position to the starting position may include translating the projection 158 along the opposite side or the proximal side of the leaf spring 164 toward the first end of the leaf spring 164, which may further direct the projection 158 toward and/or into engagement with the second guide member 162 and/or the first end of the second guide member 162. In some embodiments, the projection 158 may translate along a proximal facing surface of the second guide member 162 toward a second end of the second guide member 162 opposite the first end as the actuation mechanism 150 is returned and/or reset from the ending position toward the starting position, as seen in FIGS. 21-22. The second guide member 162 may cooperate with the projection 158 to prevent contact between the plurality of teeth 155 and the pinion 172 as the actuation mechanism 150 is returned and/or reset from the ending position toward the starting position. As such, the second guide member 162 may cooperate with the projection 158 to maintain the rack 156 disengaged from the pinion 172 and/or to maintain the actuation mechanism 150 disengaged from the threaded rod 130 as the actuation mechanism 150 is returned and/or reset from the ending position toward the starting position. In at least some embodiments, the threaded rod 130 does not rotate while resetting the actuation mechanism 150 toward and/or to the starting position.

In at least some embodiments, after reaching the ending position, the actuation mechanism 150 may be configured to automatically return to the starting position, thereby resetting the actuation mechanism 150 to advance another surgical anchor of the plurality of surgical anchors 200 or the plurality of surgical anchors 300 out of the lumen 120 and/or the distal end 112 of the elongate shaft 110 during a subsequent actuation and/or a subsequent activation of the actuation mechanism 150.

In some embodiments, the surgical anchor delivery device 100, the trigger 152, and/or the actuation mechanism 150 may be biased toward the starting position. In some embodiments, the trigger 152 and/or the actuation mechanism 150 may be self-biased toward the starting position. In some embodiments, the surgical anchor delivery device 100 and/or the actuation mechanism 150 may include a spring engaged with the trigger 152 and/or the actuation mechanism 150. In one example, a torsion spring may be disposed within and/or in engagement with the trigger 152. The torsion spring may be engaged with the handle 140 and/or the handle housing 142 such that the torsion spring biases the trigger 152 toward the starting position. In another example, a coil spring may be disposed within the handle 140 and/or the handle housing 142, and the coil spring may be engaged with the trigger 152 to bias the trigger 152 and/or the actuation mechanism 150 toward the starting position. Other spring types and/or configurations, and/or other biasing elements, are also contemplated.

In some embodiments, the surgical anchor delivery device 100, the trigger 152, and/or the actuation mechanism 150 may include a ratcheting system or a locking system configured to prevent automatic return to the starting position prematurely. In some embodiments, as the trigger 152 and/or the actuation mechanism 150 is translated toward the ending position, the ratcheting system or the locking system may prevent reverse translation back toward the starting position. In some embodiments, the actuation mechanism 150 and/or the trigger 152 may only be translatable in a first direction (e.g., toward the ending position) until reaching the ending position and/or until the projection 158 is disposed on the proximal side of the leaf spring 164.

Once the projection 158 reaches and moves past the second end of the second guide member 162, the rack 156 may move and/or snap back toward the pinion 172 due to the tension applied to the rack 156 by the tensioning spring 190. The tension applied to the rack 156 by the tensioning spring 190 urges the rack 156 back toward and/or into engagement with the pinion 172 (e.g., back to the starting position). Once the rack 156 has returned to the starting position, thereby effectively resetting the actuation mechanism 150, the surgical anchor delivery device 100, the trigger 152, and/or the actuation mechanism 150 may then be cycled and/or activated again to advance another surgical anchor of the plurality of surgical anchors 200 or the plurality of surgical anchors 300 out of the lumen 120 and/or out the distal end 112 of the elongate shaft 110 and into the treatment site.

Figure 23:
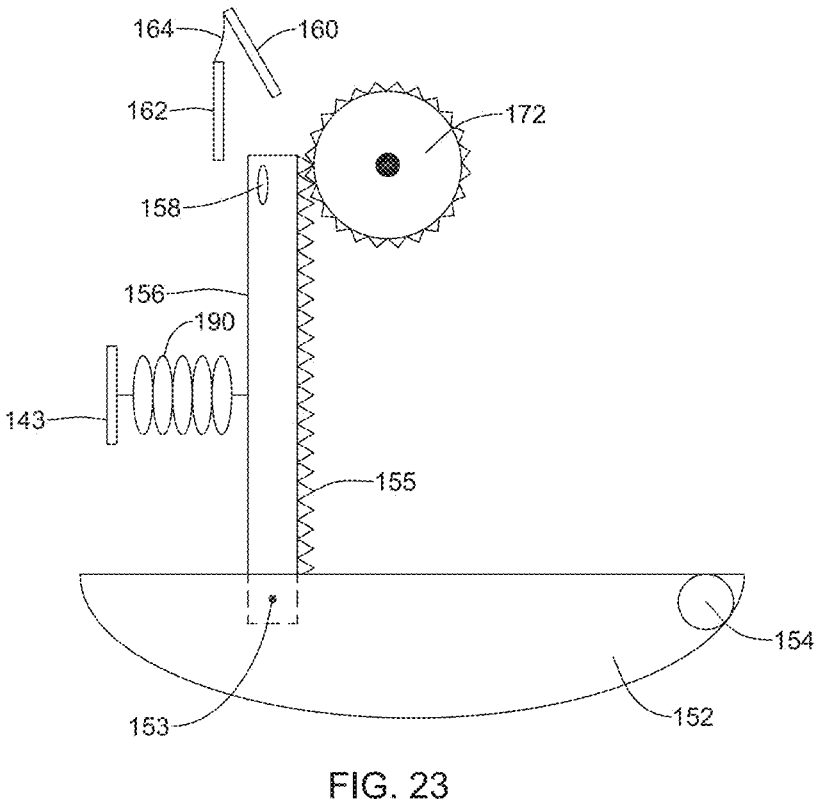
FIG. 23 illustrates selected aspects of an actuation mechanism of the surgical anchor delivery device.

FIG. 23 illustrate selected aspects of an alternative configuration of the actuation mechanism 150. The alternative configuration of FIG. 23 may be structurally and/or functionally similar to the configurations of FIGS. 18-22, except where noted. In contrast to the configuration shown in FIGS. 11 and 18, in the alternative configuration of FIG. 23 the actuation mechanism 150 may include a compression spring 192 coupled to the rack 156. The compression spring 192 may be coupled to the rack 156 at a first end and coupled to the handle 140 and/or the handle housing 142 at a second end. For the purpose of illustration only, the handle 140 and/or the handle housing 142 are not shown completely, but a portion of the handle 140 and/or the handle housing 142 is illustrated as an anchoring or coupling point 143 for the compression spring 192.

Actuating and/or activating the trigger 152 (e.g., squeezing the trigger 152, translating the trigger 152 toward the interior of the handle 140 and/or the handle housing 142, etc.) may translate the rack 156 along its length toward the ending position. As the rack 156 is translated within the handle 140 and/or the handle housing 142, the pinion 172 may be rotated by the plurality of teeth 155. Similar to FIGS. 18-22 above, the rack 156 may be substantially rigid and/or may undergo substantially no deflection as the rack 156 is translated. In some embodiments, actuation of the actuation mechanism 150 and/or translation of the rack 156 along and/or in engagement with the pinion 172 may rotate the threaded rod 130 (not shown) in a first direction. In some embodiments, the threaded rod 130 is only rotatable in the first direction.

The compression spring 192 may be disposed on a proximal side of the rack 156. The compression spring 192 may be held in compression. As such, the rack 156 may be biased toward the pinion 172, thereby keeping the plurality of teeth 155 engaged with the pinion 172. At some point during translation of the rack 156 toward the ending position, but before reaching the ending position, the projection 158 may contact and/or engage the first guide member 160. The first guide member 160 may be angled away from the pinion 172. As such, as the projection 158 moves and/or translates along the first guide member 160, the rack 156 and/or the plurality of teeth 155 may be angled away from the pinion 172 and therefore the rack 156 and/or the plurality of teeth 155 may become less engaged with the pinion 172 until the rack 156 reaches the ending position. As the rack 156 and/or the plurality of teeth 155 is angled away from the pinion 172 and the rack 156 and/or the plurality of teeth 155 become less engaged with the pinion 172, the compression spring 192 may compress and/or compressive force within the compression spring 192 may increase. While translating the projection 158 along the first guide member 160, the projection 158 may contact and/or engage a distal side of the leaf spring 164. Prior to contacting the leaf spring 164, the projection 158 may be disposed distal of the leaf spring 164.

The leaf spring 164 may deflect and/or be urged away proximally from the first guide member 160 by the projection 158 until the protrusion moves past the leaf spring 164, at which time and/or point (e.g., the ending position) the leaf spring 164 may spring and/or snap back distally into position against the first guide member 160 with the projection 158 on an opposite side or a proximal side of the leaf spring 164. After reaching the ending position, the rack 156 and/or the plurality of teeth 155 may be disengaged from the pinion 172.

In at least some embodiments, after reaching the ending position, the actuation mechanism 150 may be disengaged from the threaded rod 130 (not shown). Accordingly, after reaching the ending position, no further or additional rotation of the threaded rod 130 occurs until the actuation mechanism 150 has been reset to the starting position. Additionally, after reaching the ending position and/or after the actuation mechanism 150 disengages from the threaded rod 130, the actuation mechanism 150 may be configured to return to the starting position while disengaged from the threaded rod 130.

In some embodiments, a single actuation and/or a single activation of the actuation mechanism 150 may shift the actuation mechanism 150 from the starting position to the ending position. In at least some embodiments, shifting the actuation mechanism 150 from the starting position to the ending position may advance only one surgical anchor of the plurality of surgical anchors 200 or the plurality of surgical anchors 300 out of the lumen 120 and/or the distal end 112 of the elongate shaft 110.

Returning and/or resetting the actuation mechanism 150 from the ending position to the starting position may include translating the trigger 152, the rack 156, and/or the projection 158 toward the starting position. Returning and/or resetting the actuation mechanism 150 from the ending position to the starting position may include translating the projection 158 along the opposite side or the proximal side of the leaf spring 164 toward the first end of the leaf spring 164, which may further direct the projection 158 toward and/or into engagement with the second guide member 162 and/or the first end of the second guide member 162. In some embodiments, the projection 158 may translate along a proximal facing surface of the second guide member 162 toward a second end of the second guide member 162 opposite the first end as the actuation mechanism 150 is returned and/or reset from the ending position toward the starting position. The second guide member 162 may cooperate with the projection 158 to prevent contact between the plurality of teeth 155 and the pinion 172 as the actuation mechanism 150 is returned and/or reset from the ending position toward the starting position. As such, the second guide member 162 may cooperate with the projection 158 to maintain the rack 156 disengaged from the pinion 172 and/or to maintain the actuation mechanism 150 disengaged from the threaded rod 130 as the actuation mechanism 150 is returned and/or reset from the ending position toward the starting position. In at least some embodiments, the threaded rod 130 does not rotate while resetting the actuation mechanism 150 toward and/or to the starting position.

In at least some embodiments, after reaching the ending position, the actuation mechanism 150 may be configured to automatically return to the starting position, thereby resetting the actuation mechanism 150 to advance another surgical anchor of the plurality of surgical anchors 200 or the plurality of surgical anchors 300 out of the lumen 120 and/or the distal end 112 of the elongate shaft 110 during a subsequent actuation and/or a subsequent activation of the actuation mechanism 150.

In some embodiments, the surgical anchor delivery device 100, the trigger 152, and/or the actuation mechanism 150 may be biased toward the starting position. In some embodiments, the trigger 152 and/or the actuation mechanism 150 may be self-biased toward the starting position. In some embodiments, the surgical anchor delivery device 100 and/or the actuation mechanism 150 may include a spring engaged with the trigger 152 and/or the actuation mechanism 150. In one example, a torsion spring may be disposed within and/or in engagement with the trigger 152. The torsion spring may be engaged with the handle 140 and/or the handle housing 142 such that the torsion spring biases the trigger 152 toward the starting position. In another example, a coil spring may be disposed within the handle 140 and/or the handle housing 142, and the coil spring may be engaged with the trigger 152 to bias the trigger 152 and/or the actuation mechanism 150 toward the starting position. Other spring types and/or configurations, and/or other biasing elements, are also contemplated.

In some embodiments, the surgical anchor delivery device 100, the trigger 152, and/or the actuation mechanism 150 may include a ratcheting system or a locking system configured to prevent automatic return to the starting position prematurely. In some embodiments, as the trigger 152 and/or the actuation mechanism 150 is translated toward the ending position, the ratcheting system or the locking system may prevent reverse translation back toward the starting position. In some embodiments, the actuation mechanism 150 and/or the trigger 152 may only be translatable in a first direction (e.g., toward the ending position) until reaching the ending position and/or until the projection 158 is disposed on the proximal side of the leaf spring 164.

Once the projection 158 reaches and moves past the second end of the second guide member 162, the rack 156 may move and/or snap back toward the pinion 172 due to the compressive force applied to the rack 156 by the compression spring 192. The compressive force applied to the rack 156 by the compression spring 192 urges the rack 156 back toward and/or into engagement with the pinion 172 (e.g., back to the starting position). Once the rack 156 has returned to the starting position, thereby effectively resetting the actuation mechanism 150, the surgical anchor delivery device 100, the trigger 152, and/or the actuation mechanism 150 may then be cycled and/or activated again to advance another surgical anchor of the plurality of surgical anchors 200 or the plurality of surgical anchors 300 out of the lumen 120 and/or out the distal end 112 of the elongate shaft 110 and into the treatment site.

FIGS. 24-29 illustrate selected aspects related to the operation of the surgical anchor delivery device 100 and/or the actuation mechanism 150 and/or various embodiments and/or configurations thereof. It should be noted that not all features are shown, and the illustrated aspects are shown in a highly schematic manner for ease of illustration and understanding.

Figure 24:
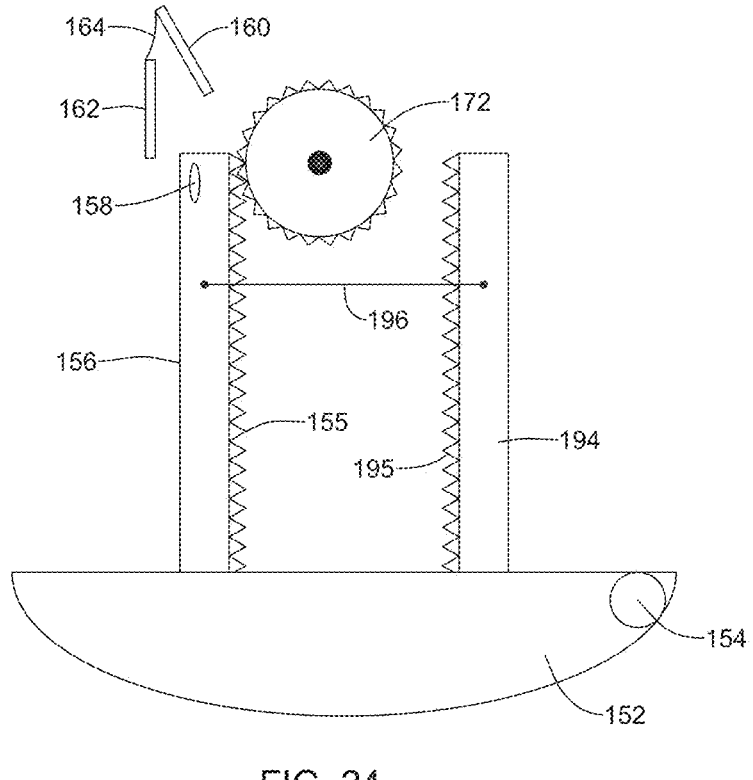
FIGS. 24-29 illustrate selected aspects of an actuation mechanism of the surgical anchor delivery device.

FIG. 24 shows the trigger 152 and the pivot point 154 where the trigger 152 is coupled to the handle 140 and/or the handle housing 142 (not shown). The rack 156 extends away from the trigger 152 and includes the plurality of teeth 155 extending in a distal direction. Other configurations are also contemplated. The projection 158 is shown extending out of the page from the rack 156. As discussed herein, this arrangement is not absolute, and in some embodiments, the projection 158 may extend in an opposite direction (e.g., into the page) from the rack 156. The first guide member 160 and the second guide member 162 may extend from the handle 140 and/or the handle housing 142. For example, the first guide member 160 and the second guide member 162 may extend inward from the first housing member and/or the second housing member. The first guide member 160 and the second guide member 162 may serve as guides for the projection 158 as the actuation mechanism 150 is actuated and/or operated.

The surgical anchor delivery device 100 and/or the actuation mechanism 150 may further comprise a second rack 194 including a second plurality of teeth 195 extending in an opposite direction from the plurality of teeth 155 and/or extending toward the plurality of teeth 155. For example, if the plurality of teeth 155 extends in the distal direction, the second plurality of teeth 195 may extend in the proximal direction, and vice versa. The actuation mechanism 150 may further comprise a link 196 extending between the rack 156 and the second rack 194. In at least some embodiments, the link 196 may be rigid. In some embodiments, the second rack 194 may be substantially rigid. In some embodiments, the second rack 194 may be semi-rigid. The link 196 may be configured to maintain a generally constant spacing between the rack 156 and the second rack 194. The rack 156 and the second rack 194 may be spaced apart by a distance that is greater than a diameter of the pinion 172, such that only one of the rack 156 and the second rack 194 is engageable with the pinion 172 at a time.

It should be noted that in order to provide sufficient spacing within the handle 140 and/or the handle housing 142 for the second rack 194 to pass by and/or over the first bevel gear 174, the second bevel gear 176, etc., the first shaft (not shown) fixedly attaching the pinion 172 to the first bevel gear 174 may be extended compared to other configurations disclosed herein, thereby spacing the first bevel gear 174 farther away from the pinion 172. The second bevel gear 176, the second shaft 177, the first spur gear 178, etc. may be offset and/or sized differently to maintain the necessary engagement with the first bevel gear 174, the second spur gear 180, etc. while permitting the second rack 194 to pass by and/or pass over them without contact and/or interference.

Figure 26:
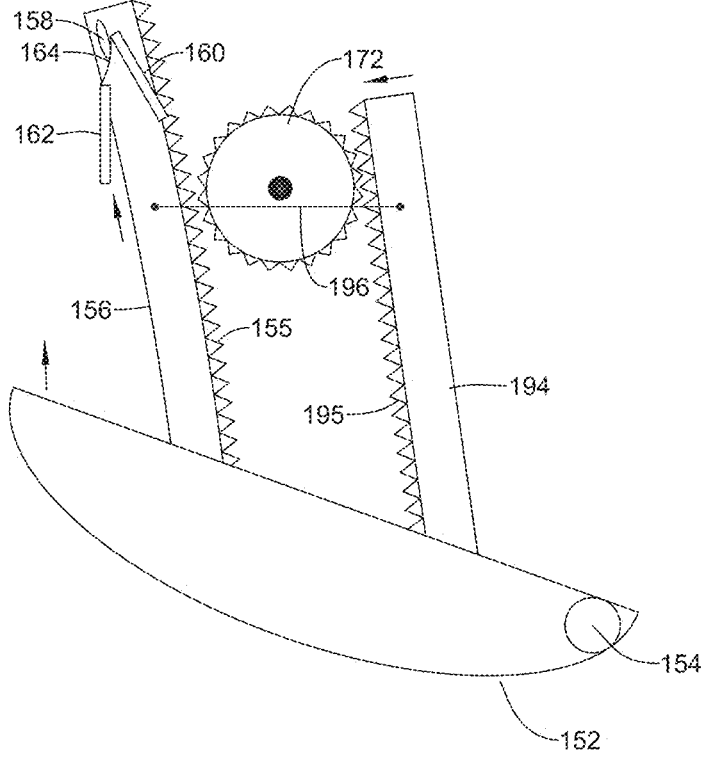

In some embodiments, the actuation mechanism 150 may be configured to shift between a starting position (e.g., FIG. 24) and an ending position (e.g., FIG. 26). In the starting position, the plurality of teeth 155 of the rack 156 may be engaged with the pinion 172 (e.g., teeth extending radially outward from the pinion 172) and the second plurality of teeth 195 of the second rack 194 may be disengaged from the pinion 172.

Figure 25:
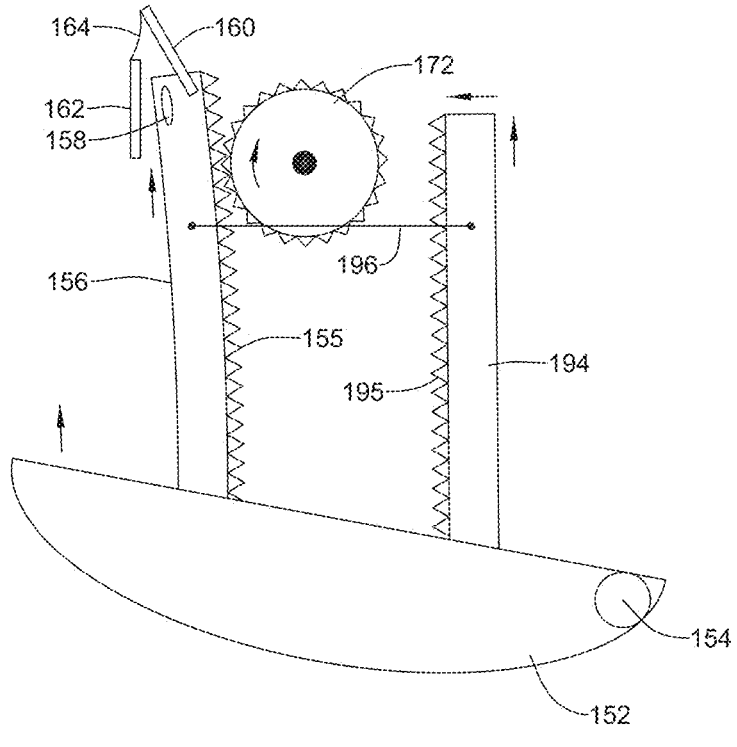

Actuating and/or activating the trigger 152 (e.g., squeezing the trigger 152, translating the trigger 152 toward the interior of the handle 140 and/or the handle housing 142, etc.) may translate the rack 156 along its length toward the ending position. As the rack 156 is translated within the handle 140 and/or the handle housing 142, the pinion 172 may be rotated by the plurality of teeth 155, as seen in FIG. 25. In some embodiments, the rack 156 may be semi-rigid and/or may deflect away from the pinion 172 as the rack 156 is translated relative to the pinion 172, as also seen in FIG. 25. This may result in an internal and/or inherent spring bias within the rack 156 that urges the rack 156 toward a straightened configuration. As such, the rack 156 may be self-biased toward the pinion 172, thereby keeping the plurality of teeth 155 engaged with the pinion 172. In some embodiments, actuation of the actuation mechanism 150 and/or translation of the rack 156 along and/or in engagement with the pinion 172 may rotate the threaded rod 130 (not shown) in a first direction. In some embodiments, the threaded rod 130 is only rotatable in the first direction. As the rack 156 deflects away from the pinion 172, the second rack 194 may be pulled and/or translated toward the pinion 172 by the link 196, as seen in FIG. 25.

At some point during translation of the rack 156 toward the ending position, but before reaching the ending position, the projection 158 may contact and/or engage the first guide member 160. The first guide member 160 may be angled away from the pinion 172. As such, as the projection 158 moves and/or translates along the first guide member 160, the rack 156 and/or the plurality of teeth 155 may be angled away from the pinion 172 and therefore the rack 156 and/or the plurality of teeth 155 may become less engaged with the pinion 172 until the rack 156 reaches the ending position, seen in FIG. 26. When the rack 156 reaches the ending position, the second plurality of teeth 195 of the second rack 194 becomes engaged with the pinion 172, as seen in FIG. 26.

While translating the projection 158 along the first guide member 160, the projection 158 may contact and/or engage a distal side of the leaf spring 164. Prior to contacting the leaf spring 164, the projection 158 may be disposed distal of the leaf spring 164.

The leaf spring 164 may deflect and/or be urged away proximally from the first guide member 160 by the projection 158 until the protrusion moves past the leaf spring 164, at which time and/or point (e.g., the ending position) the leaf spring 164 may spring and/or snap back distally into position against the first guide member 160 with the projection 158 on an opposite side or a proximal side of the leaf spring

164, as seen in FIG. 26. After reaching the ending position, the rack 156 and/or the plurality of teeth 155 may be disengaged from the pinion 172.

In a change from some embodiments, after reaching the ending position, the actuation mechanism 150 may remain engaged from the threaded rod 130 (not shown) via the second rack 194. Accordingly, after reaching the ending position, further and/or additional rotation of the threaded rod 130 in the first direction continues to occur until the actuation mechanism 150 has been reset to the starting position. After reaching the ending position, the actuation mechanism 150 may be configured to return to the starting position while engaged with the threaded rod 130. This may permit additional advancement of the plurality of surgical anchors 200 or the plurality of surgical anchors 300 toward the distal end 112 of the elongate shaft 110. For example, after reaching the ending position, the actuation mechanism 150 may be configured to return to the starting position while simultaneously advancing a successive surgical anchor of the plurality of surgical anchors 200 or the plurality of surgical anchors 300 toward the distal end 112 of the elongate shaft 110 without rotating any of the plurality of surgical anchors 200 or the plurality of surgical anchors 300 relative to the elongate shaft 110. In some embodiments, this arrangement may permit greater spacing between adjacent and/or successive surgical anchors within the elongate shaft 110. In some instances, greater spacing between adjacent and/or successive surgical anchors may reduce opportunities and/or chances of misfires and/or jams.

In some embodiments, a single actuation and/or a single activation of the actuation mechanism 150 may shift the actuation mechanism 150 from the starting position to the ending position. In at least some embodiments, shifting the actuation mechanism 150 from the starting position to the ending position may advance only one surgical anchor of the plurality of surgical anchors 200 or the plurality of surgical anchors 300 out of the lumen 120 and/or the distal end 112 of the elongate shaft 110.

Figure 27:
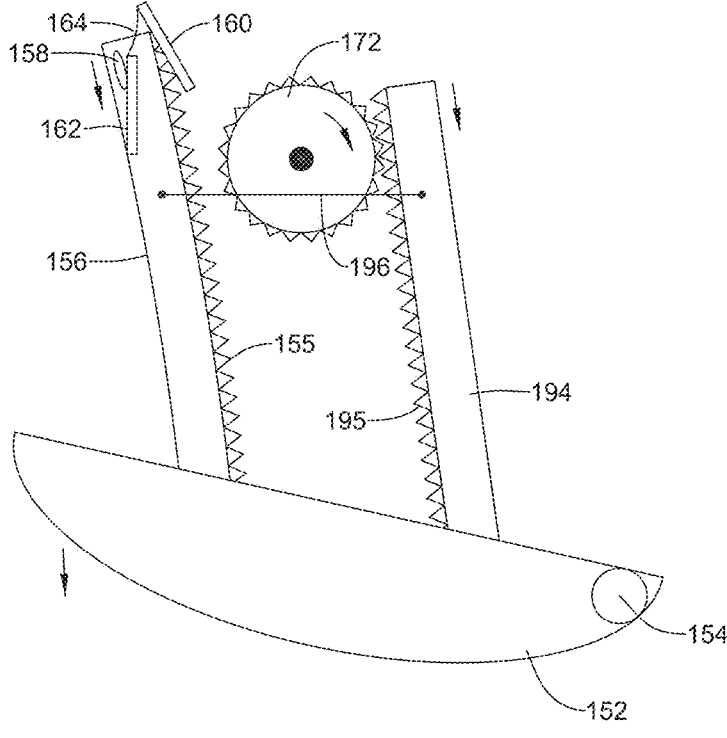
Figure 28:
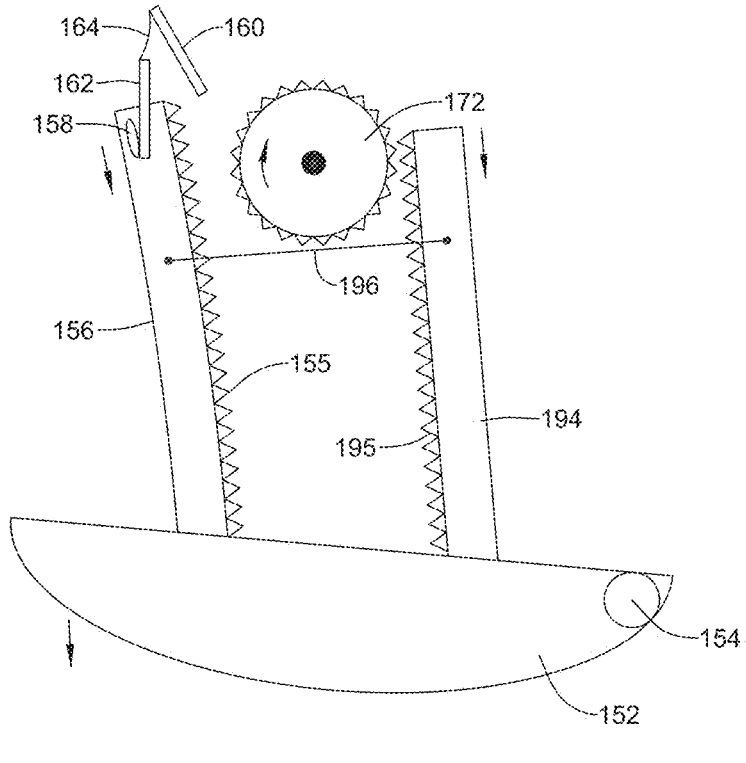

Returning and/or resetting the actuation mechanism 150 from the ending position to the starting position may include translating the trigger 152, the rack 156, and/or the projection 158 toward the starting position. Returning and/or resetting the actuation mechanism 150 from the ending position to the starting position may include translating the projection 158 along the opposite side or the proximal side of the leaf spring 164 toward the first end of the leaf spring 164, which may further direct the projection 158 toward and/or into engagement with the second guide member 162 and/or the first end of the second guide member 162. In some embodiments, the projection 158 may translate along a proximal facing surface of the second guide member 162 toward a second end of the second guide member 162 opposite the first end as the actuation mechanism 150 is returned and/or reset from the ending position toward the starting position, as seen in FIGS. 27-28. The second guide member 162 may cooperate with the projection 158 to prevent contact between the plurality of teeth 155 and the pinion 172 as the actuation mechanism 150 is returned and/or reset from the ending position toward the starting position, while the link 196 pulls and/or biases the second rack 194 into engagement with the pinion 172. As such, the second guide member 162 may cooperate with the projection 158 to maintain the rack 156 disengaged from the pinion 172 and to maintain the second rack 194 in engagement with the pinion 172 as the actuation mechanism 150 is returned and/or reset from the ending position toward the starting position. In at least some embodiments, the threaded rod 130 continues to rotate in the first direction while resetting the actuation mechanism 150 toward and/or to the starting position.

In at least some embodiments, after reaching the ending position, the actuation mechanism 150 may be configured to automatically return to the starting position, thereby resetting the actuation mechanism 150 to advance another surgical anchor of the plurality of surgical anchors 200 or the plurality of surgical anchors 300 out of the lumen 120 and/or the distal end 112 of the elongate shaft 110 during a subsequent actuation and/or a subsequent activation of the actuation mechanism 150. In some embodiments, resetting the actuation mechanism 150 may be configured to advance a subsequent or successive surgical anchor of the plurality of surgical anchors 200 or the plurality of surgical anchors 300 toward the distal end 112 of the elongate shaft 110 to prepare the subsequent or successive surgical anchor for implantation during the next actuation and/or cycle of the actuation mechanism 150.

In some embodiments, the surgical anchor delivery device 100, the trigger 152, and/or the actuation mechanism 150 may be biased toward the starting position. In some embodiments, the trigger 152 and/or the actuation mechanism 150 may be self-biased toward the starting position. In some embodiments, the surgical anchor delivery device 100 and/or the actuation mechanism 150 may include a spring engaged with the trigger 152 and/or the actuation mechanism 150. In one example, a torsion spring may be disposed within and/or in engagement with the trigger 152. The torsion spring may be engaged with the handle 140 and/or the handle housing 142 such that the torsion spring biases the trigger 152 toward the starting position. In another example, a coil spring may be disposed within the handle 140 and/or the handle housing 142, and the coil spring may be engaged with the trigger 152 to bias the trigger 152 and/or the actuation mechanism 150 toward the starting position. Other spring types and/or configurations, and/or other biasing elements, are also contemplated.

In some embodiments, the surgical anchor delivery device 100, the trigger 152, and/or the actuation mechanism 150 may include a ratcheting system or a locking system configured to prevent automatic return to the starting position prematurely. In some embodiments, as the trigger 152 and/or the actuation mechanism 150 is translated toward the ending position, the ratcheting system or the locking system may prevent reverse translation back toward the starting position. In some embodiments, the actuation mechanism 150 and/or the trigger 152 may only be translatable in a first direction (e.g., toward the ending position) until reaching the ending position and/or until the projection 158 is disposed on the proximal side of the leaf spring 164.

Figure 29:
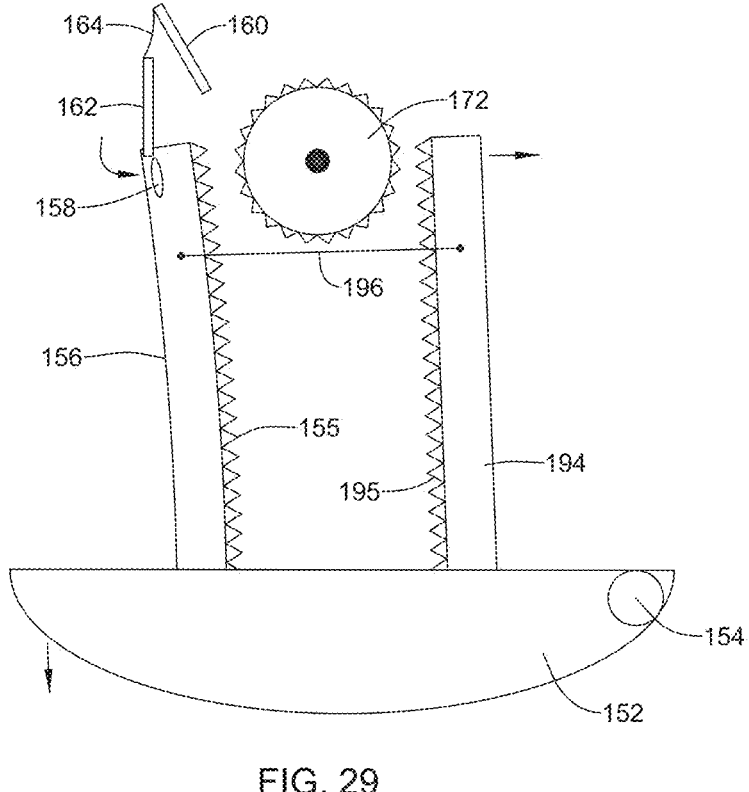

Once the projection 158 reaches and moves past the second end of the second guide member 162, the rack 156 may move and/or snap back toward the pinion 172 due to the internal and/or inherent spring bias in the rack 156, as seen in FIG. 29. The internal and/or inherent spring bias in the rack 156 urges the rack 156 back toward the straightened configuration and/or into engagement with the pinion 172 (e.g., back to the starting position). Once the rack 156 has returned to the starting position, thereby effectively resetting the actuation mechanism 150, the surgical anchor delivery device 100, the trigger 152, and/or the actuation mechanism 150 may then be cycled and/or activated again to advance another surgical anchor of the plurality of surgical anchors 200 or the plurality of surgical anchors 300 out of the lumen 120 and/or out the distal end 112 of the elongate shaft 110 and into the treatment site.

In some or all configurations disclosed herein, the actuation mechanism 150 may be designed to cyclically advance the plurality of surgical anchors 200 or the plurality of surgical anchors 300 distally along the threaded rod 130 such that the plurality of surgical anchors 200 or the plurality of surgical anchors 300 may be sequentially deployed out of the lumen 120 and/or the distal end 112 of the elongate shaft 110.

A method of delivering the plurality of surgical anchors 200 or the plurality of surgical anchors 300 to a treatment site may comprise advancing the distal end 112 of the elongate shaft 110 of the surgical anchor delivery device 100 to a first location at the treatment site, as seen schematically in FIG. 1. As discussed herein, the plurality of surgical anchors 200 or the plurality of surgical anchors 300 may be disposed within the lumen 120 and/or the elongate shaft 110 of the surgical anchor delivery device 100 prior to advancing the distal end 112 of the elongate shaft 110 to the first location.

The method may comprise rotating the threaded rod 130 disposed within the elongate shaft 110 in a first direction to advance a first surgical anchor of the plurality of surgical anchors 200 or the plurality of surgical anchors 300 out of the lumen 120 and/or out of the distal end 112 of the elongate shaft 110 without rotating the first surgical anchor within and/or relative to the elongate shaft 110. In some embodiments, the method may comprise rotating the threaded rod 130 relative to the elongate shaft 110 in the first direction to advance the first surgical anchor of the plurality of surgical anchors 200 or the plurality of surgical anchors 300 out of the lumen 120 and/or out of the distal end 112 of the elongate shaft 110 without rotating the first surgical anchor within and/or relative to the elongate shaft 110.

In at least some embodiments, rotating the threaded rod 130 to advance the first surgical anchor may include shifting the actuation mechanism 150 of the surgical anchor delivery device 100 from the starting position to the ending position. In some embodiments, shifting the actuation mechanism 150 of the surgical anchor delivery device 100 from the starting position to the ending position may advance the plurality of surgical anchors 200 or the plurality of surgical anchors 300 within the lumen 120 and/or within the elongate shaft 110 toward the distal end 112 of the elongate shaft 110 to place another surgical anchor of the plurality of surgical anchors 200 or the plurality of surgical anchors 300 in position adjacent the distal end 112 of the elongate shaft 110 for subsequent deployment. In some embodiments, the plurality of surgical anchors 200 or the plurality of surgical anchors 300 only advance toward the distal end 112 of the elongate shaft 110 when the threaded rod 130 is rotated.

The method may comprise repositioning the surgical anchor delivery device 100 and/or the distal end 112 of the elongate shaft 110 to a second position at the treatment site, and rotating the threaded rod 130 disposed within the elongate shaft 110 in the first direction to advance a second surgical anchor of the plurality of surgical anchors 200 or the plurality of surgical anchors 300 out of the lumen 120 and/or out of the distal end 112 of the elongate shaft 110 without rotating the second surgical anchor within and/or relative to the elongate shaft 110. In some embodiments, the method may comprise rotating the threaded rod 130 relative to the elongate shaft 110 in the first direction to advance the second surgical anchor of the plurality of surgical anchors 200 or the plurality of surgical anchors 300 out of the lumen 120 and/or out of the distal end 112 of the elongate shaft 110 without rotating the second surgical anchor within and/or relative to the elongate shaft 110.

In at least some embodiments, rotating the threaded rod 130 to advance the second surgical anchor may include shifting the actuation mechanism 150 of the surgical anchor delivery device 100 from the starting position to the ending position. In some embodiments, shifting the actuation mechanism 150 of the surgical anchor delivery device 100 from the starting position to the ending position may advance the plurality of surgical anchors 200 or the plurality of surgical anchors 300 within the lumen 120 and/or within the elongate shaft 110 toward the distal end 112 of the elongate shaft 110 to place another surgical anchor of the plurality of surgical anchors 200 or the plurality of surgical anchors 300 in position adjacent the distal end 112 of the elongate shaft 110 for subsequent deployment. In some embodiments, the plurality of surgical anchors 200 or the plurality of surgical anchors 300 only advance toward the distal end 112 of the elongate shaft 110 when the threaded rod 130 is rotated.

In some embodiments, the method may comprise, after rotating the threaded rod disposed within the elongate shaft 110 in the first direction to advance the first surgical anchor of the plurality of surgical anchors 200 or the plurality of surgical anchors 300 out of the lumen 120 and/or out of the distal end 112 of the elongate shaft 110, resetting the actuation mechanism 150 from the ending position to the starting position before rotating the threaded rod 130 relative to the elongate shaft 110 in the first direction to advance the second surgical anchor of the plurality of surgical anchors 200 or the plurality of surgical anchors 300 out of the lumen 120 and/or out of the distal end 112 of the elongate shaft 110 without rotating the second surgical anchor within and/or relative to the elongate shaft 110. In some embodiments, the threaded rod 130 does not rotate within and/or relative to the elongate shaft 110 while resetting the actuation mechanism 150 from the ending position to the starting position. In some embodiments, the threaded rod 130 rotates in the first direction within and/or relative to the elongate shaft 110 while resetting the actuation mechanism 150 from the ending position to the starting position The cycle may continue and/or be repeated with a user repositioning the surgical anchor delivery device 100 and deploying additional surgical anchors of the plurality of surgical anchors 200 or the plurality of surgical anchors 300 until all surgical anchors required or present in the surgical anchor delivery device 100 are deployed, without having to remove the surgical anchor delivery device 100 from the treatment site.

The materials that can be used for the various components of the medical devices, systems, and various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the surgical anchor(s), the surgical anchor delivery device, the elongate shaft, the actuation mechanism, etc., and/or elements or components thereof.

In some embodiments, the system and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(al-kylene ether) phthalate and/or other polyester elastomers such as HYTREL®), polyamide (for example, DURE-THAN® or CRISTAMID®), elastomeric polyamides, block polyamide/ethers, polyether block amide (PEBA, for example PEBAX®), ethylene vinyl acetate copolymers (EVA), silicones, polyethylene (PE), MARLEX® high-den-sity polyethylene, MARLEX® low-density polyethylene, linear low density polyethylene (for example REXELL®), polyester, polybutylene terephthalate (PBT), polyethylene terephthalate (PET), polytrimethylene terephthalate, poly-ethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, poly-styrene, epoxy, polyvinylidene chloride (PVdC), poly(sty-rene-b-isobutylene-b-styrene) (for example, SIBS and/or SIBS 50A), polycarbonates, polyurethane silicone copoly-mers (for example, Elast-Eon® or ChronoSil®), biocom-patible polymers, other suitable materials, or mixtures, com-binations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304 and/or 316 stainless steel and/or variations thereof; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chro-mium-molybdenum alloys (e.g., UNS: R30003 such as ELGILOY®, PHYNOX®, and the like); platinum enriched stainless steel; titanium; platinum; palladium; gold; combi-nations thereof; or any other suitable material.

In some embodiments, portions or all of the system and/or components thereof may be doped with, made of, or other-wise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in deter-mining the location of the system. Some examples of radiopaque materials can include, but are not limited to, gold, platinum, palladium, tantalum, tungsten alloy, polymer material loaded with a radiopaque filler, and the like. Addi-tionally, other radiopaque marker bands and/or coils may also be incorporated into the design of the system to achieve the same result.

In some embodiments, a degree of Magnetic Resonance Imaging (MRI) compatibility is imparted into the system.

For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system and/or other elements disclosed herein may include and/or be treated with a suitable therapeutic agent. Some examples of suitable thera-peutic agents may include anti-thrombogenic agents (such as heparin, heparin derivatives, urokinase, and PPack (dextro-phenylalanine proline arginine chloromethyl ketone)); anti-protein and/or anti-bacterial agents (such as 2-methacryloy-loxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasa-lazine, and mesalamine); antineoplastic/antiproliferative/ anti-mitotic agents (such as paclitaxel, 5-fluorouracil, cis-platin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antago-nists, transcriptional activators, and translational promot-ers); vascular cell growth inhibitors (such as growth factor inhibitors, growth factor receptor antagonists, transcrip-tional repressors, translational repressors, replication inhibi-tors, inhibitory antibodies, antibodies directed against growth factors, bifunctional molecules consisting of a growth factor and a cytotoxin, bifunctional molecules con-sisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endog-enous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A surgical anchor delivery device, comprising:
an elongate shaft having a lumen extending to a distal end of the elongate shaft;
a plurality of surgical anchors disposed within the lumen; and a threaded rod disposed within the elongate shaft and threadably engaged with the plurality of surgical anchors;

wherein rotation of the threaded rod advances the plurality of surgical anchors within the lumen toward the distal end of the elongate shaft without rotating the plurality of surgical anchors relative to the elongate shaft.

2. The surgical anchor delivery device of claim 1, wherein the plurality of surgical anchors is prevented from rotating relative to the elongate shaft.

3. The surgical anchor delivery device of claim 2, wherein the lumen includes a noncircular cross-sectional shape.

4. The surgical anchor delivery device of claim 3, wherein each surgical anchor of the plurality of surgical anchors includes a noncircular perimeter shape.

5. The surgical anchor delivery device of claim 2, wherein each surgical anchor of the plurality of surgical anchors includes a tab extending radially outward from a peripheral edge of the anchor.

6. The surgical anchor delivery device of claim 5, wherein the elongate shaft includes a channel extending longitudinally along a wall of the elongate shaft and opening radially inwards;

wherein the tab is configured to extend into the channel when the plurality of surgical anchors is disposed within the lumen.

7. The surgical anchor delivery device of claim 1, wherein the plurality of surgical anchors is configured to slide distally within the lumen in response to rotation of the threaded rod.

8. The surgical anchor delivery device of claim 1, wherein rotation of the threaded rod is configured to advance the plurality of surgical anchors out of the lumen.

9. The surgical anchor delivery device of claim 8, wherein rotation of the threaded rod is configured to drive at least one barb extending distally from each surgical anchor of the plurality of surgical anchors into a target tissue.

10. A surgical anchor delivery device, comprising:
a handle including an actuation mechanism;
an elongate shaft extending from the handle, the elongate shaft having a lumen extending to a distal end of the elongate shaft;
a plurality of surgical anchors disposed within the lumen; and
a threaded rod disposed within the lumen and threadably engaged with the plurality of surgical anchors;
wherein rotation of the threaded rod advances the plurality of surgical anchors within the lumen toward the distal end of the elongate shaft without rotating the plurality of surgical anchors relative to the elongate shaft;
wherein the actuation mechanism is configured to rotate the threaded rod.

11. The surgical anchor delivery device of claim 10, wherein the actuation mechanism is configured to rotate the threaded rod in only a single direction.

12. The surgical anchor delivery device of claim 10, wherein the actuation mechanism is configured to shift between a starting position and an ending position;
wherein shifting the actuation mechanism from the starting position to the ending position advances only one surgical anchor of the plurality of surgical anchors out of the lumen.

13. The surgical anchor delivery device of claim 12, wherein after reaching the ending position, the actuation mechanism disengages from the threaded rod and the actuation mechanism is configured to return to the starting position while disengaged from the threaded rod.

14. The surgical anchor delivery device of claim 12, wherein after reaching the ending position, the actuation mechanism is configured to return to the starting position while simultaneously advancing a successive surgical anchor of the plurality of surgical anchors toward the distal end of the elongate shaft without rotating any of the plurality of surgical anchors relative to the elongate shaft.

* * * * *